(12) United States Patent
Kato et al.

(10) Patent No.: US 9,131,889 B2
(45) Date of Patent: Sep. 15, 2015

(54) COGNITIVE IMPAIRMENT DETERMINATION APPARATUS, COGNITIVE IMPAIRMENT DETERMINATION SYSTEM AND PROGRAM

(75) Inventors: Shohei Kato, Nagoya (JP); Hidetoshi Endo, Inazawa (JP)

(73) Assignee: Nagoya Institute of Technology (JP)

( * ) Notice: Subject to any disclaimer, the term of this patent is extended or adjusted under 35 U.S.C. 154(b) by 114 days.

(21) Appl. No.: 14/122,786

(22) PCT Filed: May 31, 2012

(86) PCT No.: PCT/JP2012/064237
§ 371 (c)(1),
(2), (4) Date: Nov. 27, 2013

(87) PCT Pub. No.: WO2012/165602
PCT Pub. Date: Dec. 6, 2012

(65) Prior Publication Data
US 2014/0107494 A1   Apr. 17, 2014

(30) Foreign Application Priority Data

May 31, 2011   (JP) .................................. 2011-121241

(51) Int. Cl.
*A61B 5/00* (2006.01)
*A61B 5/026* (2006.01)

(52) U.S. Cl.
CPC .............. *A61B 5/4088* (2013.01); *A61B 5/0042* (2013.01); *A61B 5/0261* (2013.01); *A61B 5/4064* (2013.01); *A61B 5/7267* (2013.01); *A61B5/725* (2013.01); *A61B 5/7207* (2013.01); *A61B 2576/026* (2013.01)

(58) Field of Classification Search
CPC ........... A61B 2576/026; A61B 5/0042; A61B 5/0261; A61B 5/4064; A61B 5/4088; A61B 5/7207; A61B 5/725; A61B 5/7267
See application file for complete search history.

(56) References Cited

U.S. PATENT DOCUMENTS

2005/0177033 A1   8/2005   Kawasaki
2007/0055118 A1   3/2007   Kawasaki et al.
(Continued)

FOREIGN PATENT DOCUMENTS

JP   2003-275191 A   9/2003
JP   2011-255106 A   12/2011
(Continued)

OTHER PUBLICATIONS

Folstein, M. F., et al.,"Mini-Mental State: A Practical Method for Grading the Cognitive State of Patients for the Clinician" J. Psychiat. Res., 1975, pp. 189-198, vol. 12, No. 3.
(Continued)

*Primary Examiner* — Michael Rozanski
(74) *Attorney, Agent, or Firm* — Banner & Witcoff, Ltd.

(57) ABSTRACT

Cerebral blood flow data during cognitive task execution is measured using a functional near infrared spectroscopy method, then characteristic amount extraction is performed after performing primitive analysis on the measured cerebral blood flow data. Then, by using the extracted characteristic amounts and a pre-built model for employing in determination of cognitive impairment, automatic determination is made into clinical diagnostic groups of normal (NC), mild cognitive impairment (MCI) and Alzheimer's disease (AD). It is thereby possible to perform cognitive impairment determination that is suitable for mass early stage screening of elderly people.

10 Claims, 15 Drawing Sheets

(56) References Cited

U.S. PATENT DOCUMENTS

2009/0118602 A1     5/2009    Kawasaki et al.
2010/0256468 A1    10/2010    Tanaka et al.

FOREIGN PATENT DOCUMENTS

| | | |
|---|---|---|
| WO | 2005/025421 A1 | 3/2005 |
| WO | 2005/096951 A1 | 10/2005 |
| WO | 2006/132313 A1 | 12/2006 |
| WO | 2007/144977 A1 | 12/2007 |
| WO | 2008/142878 A1 | 11/2008 |

OTHER PUBLICATIONS

Katoh, S., et al.,"Development of the Revised Version of Hasegawa's Dementia Scale (HDS-R)" Japanese Journal of Geriatric Psychiatry, 1991, pp. 1339-1347, vol. 2, No. 11.

English Translation of Katoh, S., et al.,"Development of the Revised Version of Hasegawa's Dementia Scale (HDS-R)" Japanese Journal of Geriatric Psychiatry, 1991, pp. 1339-1347, vol. 2, No. 11.

Morris, J. C., "The Clinical Dementia Rating (CDR): Current Version and Scoring Rules," Neurology, 1993, pp. 2412-2414, vol. 43, No. 11.

Shohei, Koto, et al.,"A Preliminary Study of Speech Prosody-Based Relationship with HDS-R Scores Toward Early Detection of Cognitive Impairment in Elderly Using Speech Prosody" Journal of Japanese Society for Artificial Intelligence, 2011, pp. 347-352, vol. 26, No. 2.

English Translation of Shohei, Koto, et al.,"A Preliminary Study of Speech Prosody-Based Relationship with HDS-R Scores Toward Early Detection of Cognitive Impairment in Elderly Using Speech Prosody" Journal of Japanese Society for Artificial Intelligence, 2011, pp. 347-352, vol. 26, No. 2.

Zhang, D., et al.,"The Multimodal Classification of Alzheimer's Disease and Mild Cognitive Impairment," Journal of Neuroimage, 2011, pp. 856-867, vol. 55, No. 3.

FIG.5

00:00:00 — TIMELINE — 00:14:00

| 300 SECONDS | 300 SECONDS | 60 SECONDS | 60 SECONDS | 60 SECONDS | 60 SECONDS |
|---|---|---|---|---|---|
| SMALL TALK (PLACE OF BIRTH, CHILDHOOD, SCHOOL ETC.) | HDS-R HASEGAWA TEST | 1 POINT ATTENTION (REST) | RECOLLECTION METHOD 1 LISTENING | 1 POINT ATTENTION (REST) | RECOLLECTION METHOD 2 SPEAKING |

00:14:00 — TIMELINE — 00:22:30

| 60 SEC | 60 SEC | 60 SEC | 60 SEC | 60 SEC | 60 SEC | 60 SEC | 60 SEC | 60 SEC | 30 SEC. |
|---|---|---|---|---|---|---|---|---|---|
| 1 POINT ATT. (REST) | RECOLLECTION METHOD 3 SEEING | 1 POINT ATT. (REST) | WORKING MEMORY TASK 1: CATEGORY RECALL | 1 POINT ATT. (REST) | WORKING MEMORY TASK 2: READING SPAN | 1 POINT ATT. (REST) | WORKING MEMORY TASK 3: FACE RECALL | REST | |

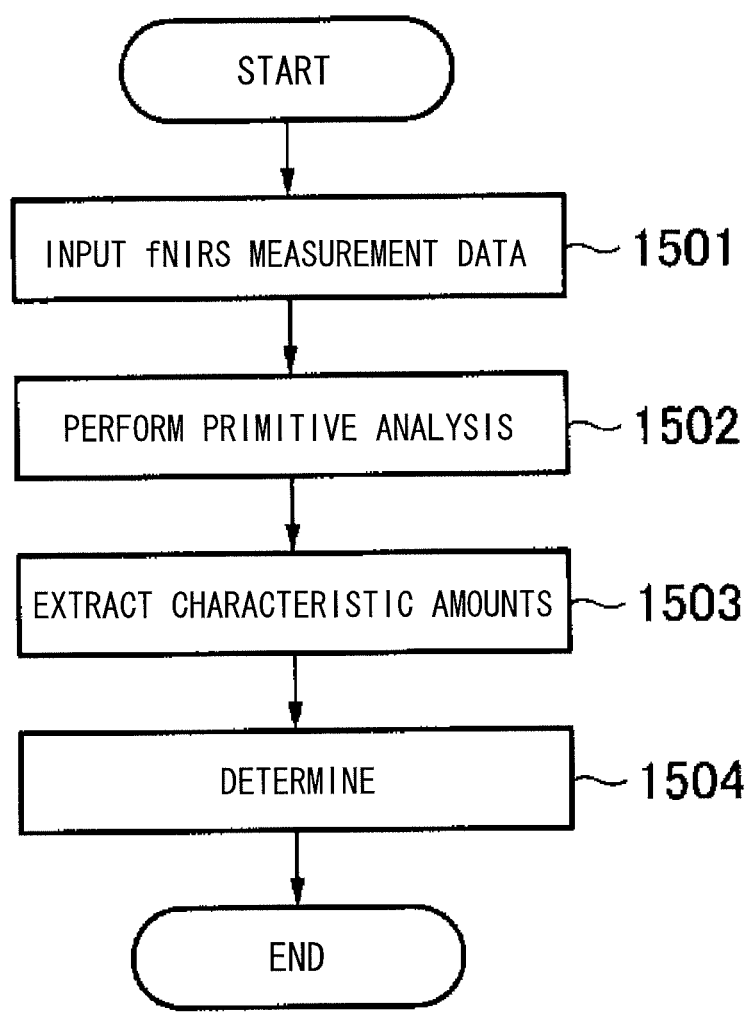

COGNITIVE IMPAIRMENT DETERMINATION APPARATUS, COGNITIVE IMPAIRMENT DETERMINATION SYSTEM AND PROGRAM

RELATED APPLICATION DATA

This application is a National Stage Application under 35 U.S.C. 371 of co-pending PCT application PCT/JP2012/064237 designating the United States and filed May 31, 2012; which claims the benefit of JP application number 2011-121241 and filed May 31, 2011 each of which are hereby incorporated by reference in their entireties.

TECHNICAL FIELD

The present invention relates to a cognitive impairment determination apparatus, and to a cognitive impairment determination system and program, and in particular to a cognitive impairment determination apparatus, a cognitive impairment determination system and program that perform determination of cognitive impairment using vital signals of a brain.

BACKGROUND ART

Currently screening for dementia includes, for example: a revised version of Hasegawa's Dementia Scale (HDS-R), as described in "Katoh, S., Simogaki, H., Onodera, A., Ueda, H., Oikawa, K., Ikeda, K., Kosaka, K., Imai, Y., and Hasegawa, K.: Development of the revised version of Hasegawa's Dementia Scale (HDS-R), Japanese Journal of Geriatric Psychiatry, Vol. 2, No. 11, pp. 1339-1347 (1991), (in Japanese)"; Mini-Mental State Examination (MMSE) as described in "Folstein, M. F., Folstein, S. E., and McHugh, P. R.: "Mini-Mental State": A practical method for grading the cognitive state of patients for the clinician, J. Psychiat. Res, Vol. 12, No. 3, pp. 189-198 (1975)"; and Clinical Dementia Rating (CDR) as described in "Morris, J. C.: The Clinical Dementia Rating (CDR): Current version and scoring rules, Neurology, Vol. 43, No. 11, pp. 2412-2414 (1993). Such dementia screening methods are similarly widely used to tests based on neurophysiology such as functional MRI (fMRI), FDG-PET, and CSF biomarkers, as described in "Zhang, D., Wang, Y., Zhou, L., Yuan, H., Shen, D., and The Alzheimer's Disease Neuroimaging Initiative: Multimodal classification of Alzheimer's disease and mild cognitive impairment, Journal of Neuroimage, Vol. 55, No. 3, pp. 856-867 (2011)".

These are performed by doctors who have received a given amount of training or clinical physicians, mainly in medical institutions.

However, in the normal outpatient scenario, although these are simple investigations, such as HDS-R, a doctor takes about 5 to 20 minutes to perform the investigation. It is accordingly pointed out that this has a negative impact on the treatment of other outpatients, with consideration given to the need to reduce the burden on doctors.

For example, known tests based on neurophysiology such as fMRI, FDG-PET and CSF biomarkers mentioned above are described in "The Alzheimer's Disease Neuroimaging Initiative: Multimodal classification of Alzheimer's disease and mild cognitive impairment, by Zhang, D., Wang, Y., Zhou, L., Yuan, H., Shen, D., and Journal of Neuroimage, Vol. 55, No. 3, pp. 856-867 (2011)". Although these tests are non-invasive, due to the many limitations, such as the difficulty of taking spinal fluid samples, radiation exposure, the large size of measurement apparatus, and the need to restrain test subjects, they are not suitable for mass early stage screening of elderly people.

If a tool could be developed that was more simple and easier to use, and also had equivalent performance or better than that of existing tools, physicians would then be able to further widen the scope of implemented screening. This would accordingly enable a contribution to be made to early stage diagnosis of dementia.

In previous research (Japanese Patent Application Laid-Open (JP-A) No. 2011-255106) and "Preliminary Study of Speech Prosody-Based Relationship with HDS-R Scores Toward Early Detection of Cognitive Impairment in Elderly Using Speech Prosody by Shohei Kato, Yuta Suzuki, Akiko Kobayashi, Toshiaki Kojima, Hidenori Itoh, Akira Homma; Transactions of the Japanese Society for Artificial Intelligence; Vol. 26; No. 2, pp. 347-352 (2011)), the present inventors have researched screening of cognitive impairment by observing spoken speech of elderly people and using speech prosodic characteristics. This technology has the advantage that, due to using only voice data, it can be implemented on anyone irrespective of location, such as at home or during a visit (in primary screening).

DISCLOSURE OF INVENTION

Technical Problem

However, the technology described in JP-A No. 2011-255106 and "Preliminary Study of Speech Prosody-Based Relationship with HDS-R Scores Toward Early Detection of Cognitive Impairment in Elderly Using Speech Prosody" by Shohei Kato et. al is limited to application as secondary screening directly conducted by specialist medical organizations due to the lack of direct measurement of cerebral function.

The present invention address the above issues, and an object thereof is to provide a cognitive impairment determination apparatus, and a cognitive impairment determination system and program suitable for early stage cerebral function related screening.

Solution to Problem

In order to achieve the above object, a cognitive impairment determination apparatus of a first aspect of the present invention includes: a data acquisition section that acquires vital signal data, at predetermined brain locations of a test subject, measured whilst being given a task that causes brain activation; a characteristic amount extraction section that extracts characteristic amounts of the vital signal data acquired by the data acquisition section; and a determination section that determines a level of cognitive impairment of the test subject based on the characteristic amount extracted by the characteristic amount extraction section and based on pre-derived data for use in determination of cognitive impairment.

A cognitive impairment determination apparatus of a second aspect of the present invention is the cognitive impairment determination apparatus of the first aspect, wherein the vital signal data is cerebral blood flow data measured from blood flow at the predetermined brain locations.

A cognitive impairment determination apparatus of a third aspect of the present invention is the cognitive impairment determination apparatus of the first aspect, wherein: the vital signal data is cerebral blood flow data from measuring hemoglobin flow rates using an NIRS device with a prefrontal region, a left temporal lobe, a right temporal lobe, a left parietal lobe and a right parietal lobe respectively serving as the predetermined brain locations.

A cognitive impairment determination apparatus of a fourth aspect of the present invention is the cognitive impairment determination apparatus of claim 1, wherein: the vital signal data is cerebral blood flow data from measuring hemoglobin flow rates for each region using an NIRS device with a right region, a central region and a left region in a prefrontal region serving as predetermined brain locations, and a specific region in a left parietal lobe and a specific region in a left temporal lobe serving as predetermined brain locations, and a specific region in a right parietal lobe and a specific region in a right temporal lobe respectively serving as predetermined brain locations.

A cognitive impairment determination apparatus of a fifth aspect of the present invention is the cognitive impairment determination apparatus of any one of the first aspect to the fourth aspect, further including: a known data acquisition section that acquires the vital signal data measured whilst plural test subjects whose levels of cognitive impairment are known are being given the task; a known data characteristic amount extraction section that extracts characteristic amounts of the vital signal data acquired by the known data acquisition section; and a determination data generation section that generates data employed in determining the cognitive impairment based on the characteristic amounts extracted by the known data characteristic amount extraction section.

A cognitive impairment determination apparatus of a sixth aspect of the present invention is the cognitive impairment determination apparatus of the fifth aspect, wherein the determination data generation section includes: a selection section that selects a characteristic amount to employ in the cognitive impairment determination from out of the characteristic amounts extracted by the known data characteristic amount extraction section; a learning section that employs as learning data the characteristic amounts selected by the selection section and the cognitive impairment level of the test subject from whom the characteristic amount was extracted to build a model for the determination section to determine a level of cognitive impairment corresponding to the characteristic amount.

A cognitive impairment determination apparatus of a seventh aspect of the present invention is the cognitive impairment determination apparatus of any one of the first aspect to the sixth aspect, further including: a primitive analysis section that performs noise removal on the input vital signal data using plural low pass filters, wherein the plural low pass filters includes a first filter employed to remove noise including noise from environmental light, a second filter employed for extracting fluctuation components including brainwaves and blood pressure, and a third filter employed to remove noise due to movement including jaw movement, and eyeball movement; wherein in the data characteristic amount extraction section, the primitive analysis section extracts, as characteristic amounts of the vital signal data, an amplitude average value, a fundamental frequency and a centroid frequency for the vital signal data from which noise has been removed using the first filter, an amplitude maximum value, an amplitude minimum value, an amplitude variance value, an amplitude average value, a fundamental frequency and a gradient of straight line approximation for the vital signal data from which noise has been removed using the third filter, an amplitude variance value of difference data between the vital signal data from which noise has been removed using the first filter and the vital signal data from which noise has been removed using the third filter, and a variance value of difference data between the vital signal data from which noise has been removed using the second filter and the vital signal data from which noise has been removed using the third filter; and the determination section performs determination of the cognitive impairment level of the test subject on the basis of the characteristic amounts extracted by the data characteristic amount extraction section.

Moreover, a cognitive impairment determination system according to an eighth aspect of the present invention includes: a determination data generation device including a known data acquisition section that acquires vital signal data at predetermined brain locations, measured whilst plural test subjects whose levels of cognitive impairment are known are being given a task that causes brain activation, a known data characteristic amount extraction section that extracts characteristic amounts of the vital signal data acquired by the known data acquisition section, and a determination data generation section that generates data employed in determining the cognitive impairment based on the characteristic amounts extracted by the known data characteristic amount extraction section; and a cognitive impairment determination apparatus that includes a data acquisition section that acquires vital signal data at a predetermined brain location of a test subject whose level of cognitive impairment is unknown measured whilst being given the task, a characteristic amount extraction section that extracts characteristic amounts of the vital signal data acquired by the data acquisition section, and a determination section that determines a level of cognitive impairment of the test subject of unknown cognitive impairment level based on the characteristic amount extracted by the characteristic amount extraction section and based on data generated by the determination data generation device.

A program according to a ninth aspect of the present invention causes a computer to function as: a data acquisition section that acquires vital signal data at predetermined brain locations of a test subject measured whilst being given a task that causes brain activation; a characteristic amount extraction section that extracts characteristic amounts of the vital signal data acquired by the data acquisition section; and a determination section that determines a level of cognitive impairment of the test subject based on the characteristic amount extracted by the characteristic amount extraction section and based on pre-derived data for use in determination of cognitive impairment.

Advantageous Effects of Invention

As explained above, according to the present invention, by acquiring vital signals of plural regions of the brain of a test subject during cognitive task execution and extracting characteristic amounts of the vital signals, the advantageous effect is exhibited of being able to determine whether or not the test subject has cognitive impairment based on these characteristic amounts and on pre-derived data for employing in cognitive impairment determination, thereby enabling early stage screening related to cognitive function.

BRIEF DESCRIPTION OF DRAWINGS

FIG. 5 is an explanatory diagram illustrating a block design employed during cerebral blood flow measurement using a cognitive impairment determination apparatus according to an exemplary embodiment.

FIG. 15 is a flow chart illustrating a third processing flow executed by a cognitive impairment determination apparatus according to an exemplary embodiment.

BEST MODE FOR CARRYING OUT THE INVENTION

Detailed explanation follows regarding an exemplary embodiment of the present invention, with reference to the drawings. Note that in the present exemplary embodiment there is no need for a particular measurement environment, and cerebral function during task execution may be measured in a natural position, with attention given to vital signals obtained from functional near-infrared spectroscopy (also referred to below as "fNIRS"). Explanation follows regarding the present exemplary embodiment in an example of the present invention applied to dementia screening performed using cerebral function measurement data from an elderly person during cognitive task test execution.

Note that fNIRS is a known technique for measuring hemoglobin flow inside a brain using near-infrared light, and the technique is non-invasive and requires little restraint of the person to be measured (referred to below as the test subject), enabling comparatively simple measurement without test environment selection.

In the present exemplary embodiment, cerebral blood flow data during cognitive task execution is measured using such functional near-infrared spectroscopy, and then based on the measured cerebral blood flow data, automatic screening is made into clinical diagnostic groups of normal (NC), mild cognitive impairment (MCI), or Alzheimer's disease (AD).

Figure 1:
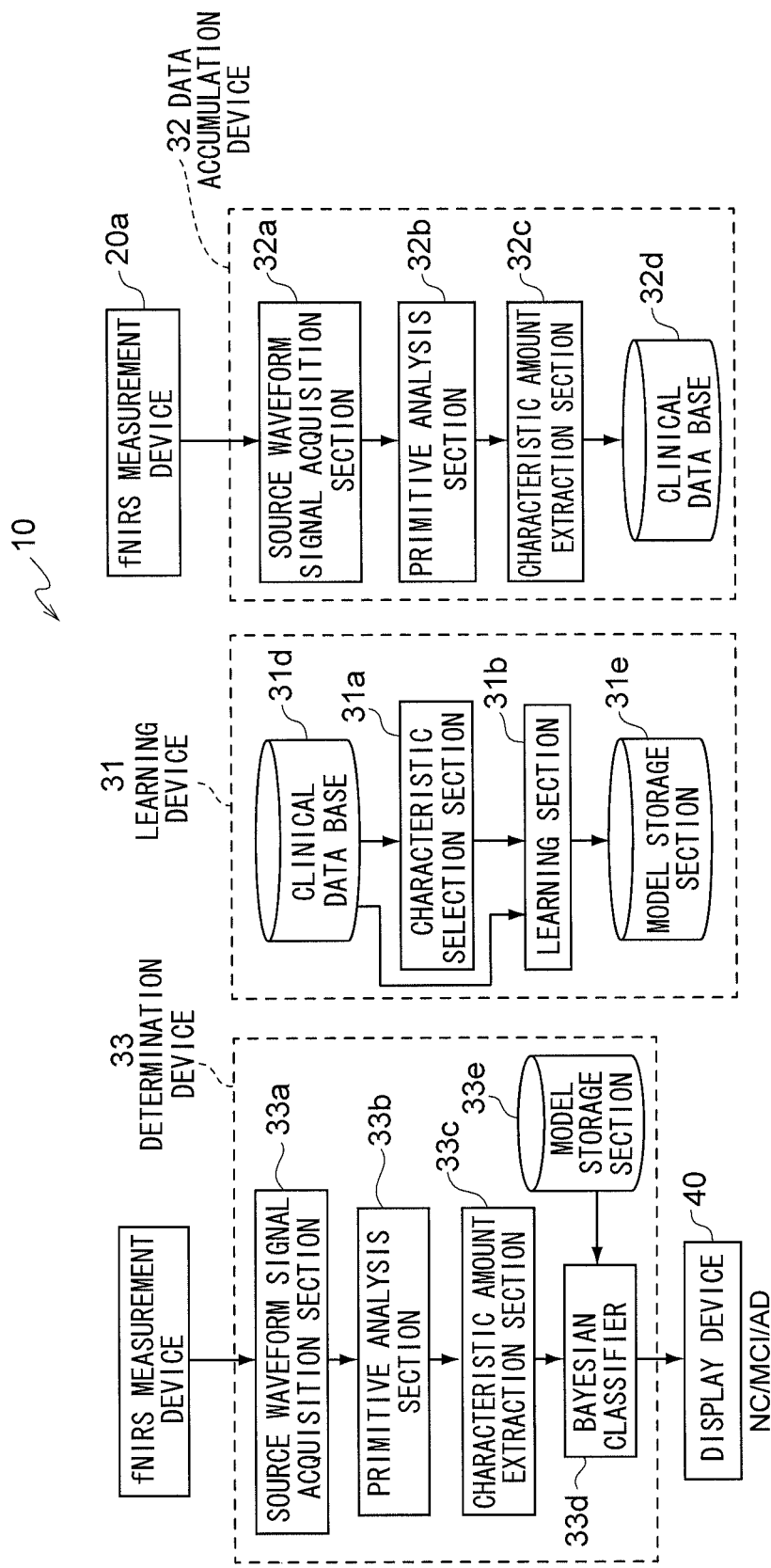
FIG. 1 is a block diagram illustrating a configuration of a cognitive impairment determination apparatus according to an exemplary embodiment.

As illustrated in FIG. 1, a cognitive impairment determination apparatus 10 according to the present exemplary embodiment is equipped with fNIRS measurement devices 20, 20a that measure cerebral blood flow data during cognitive task execution using a functional near-infrared spectroscopy method, a learning device 31 configured by a computer that executes cognitive impairment determination processing according to the present invention, a data accumulation device 32, a determination device 33, and a display device 40 that displays processing results and the like on the determination device 33.

The learning device 31, the data accumulation device 32, the determination device 33 are each equipped with a Central Processing Unit (CPU), Read Only Memory (ROM), Random Access Memory (RAM), and a Hard Disk Drive (HDD). The HDD is stored with a program the CPU employs when executing the cognitive impairment determination processing according to the present invention.

As processing functions to implement program execution, the learning device 31 is equipped with a characteristic selection section 31a, a learning section 31b, a clinical data base 31d and a model storage section 31e.

As processing functions to implement program execution, the data accumulation device 32 is equipped with a source waveform signal acquisition section 32a, a primitive analyzer section 32b, a characteristic amount extraction section 32c and a clinical data base 32d.

As processing functions to implement program execution, the determination device 33 is equipped a source waveform signal acquisition section 33a, a primitive analyzer section 33b, a characteristic amount extraction section 33c, a Bayesian classifier 33d and a model storage section 33e.

In the present exemplary embodiment, each of the data accumulation device 32 and the determination device 33 is respectively configured equipped with the source waveform signal acquisition sections 32a, 33a, the primitive analyzer sections 32b, 33b and the characteristic amount extraction sections 32c, 33c. Each of the data accumulation device 32 and the determination device 33 may be configured equipped with the same computer, and may thereby be configured with a configuration that has common source waveform signal acquisition sections 32a, 33a, common primitive analyzer sections 32b, 33b, and/or common characteristic amount extraction sections 32c, 33c.

As vital signals, the fNIRS measurement devices 20, 20a measure cerebral blood flow data of the test subject. Increased cerebral blood flow, for example as described in "Villringer, A. and Firnafl, U.: Coupling of brain activity and cerebral blood flow: basis of functional neuroimaging, Cerebrovasc. Brain Metab. Rev., Vol. 7, pp. 240-276 (1995)", reflects activation of neural activity at that brain site, and it is possible to capture changes in cerebral blood flow by measuring changes in rates of oxygenated hemoglobin (oxy-Hb) in blood fluid. Changes in the rate of oxy-Hb measured by the fNIRS measurement devices 20, 20a may therefore be taken as an index of cerebral activity.

In the present exemplary embodiment, multi-channel fNIRS measurement devices 20, 20a are employed to measure cerebral activity of the elderly people during cognitive task execution. Specifically, a near-infrared spectroscopy cerebral function imaging device FOIRE-3000® manufactured by Shimadzu Corporation is employed.

Figure 2:
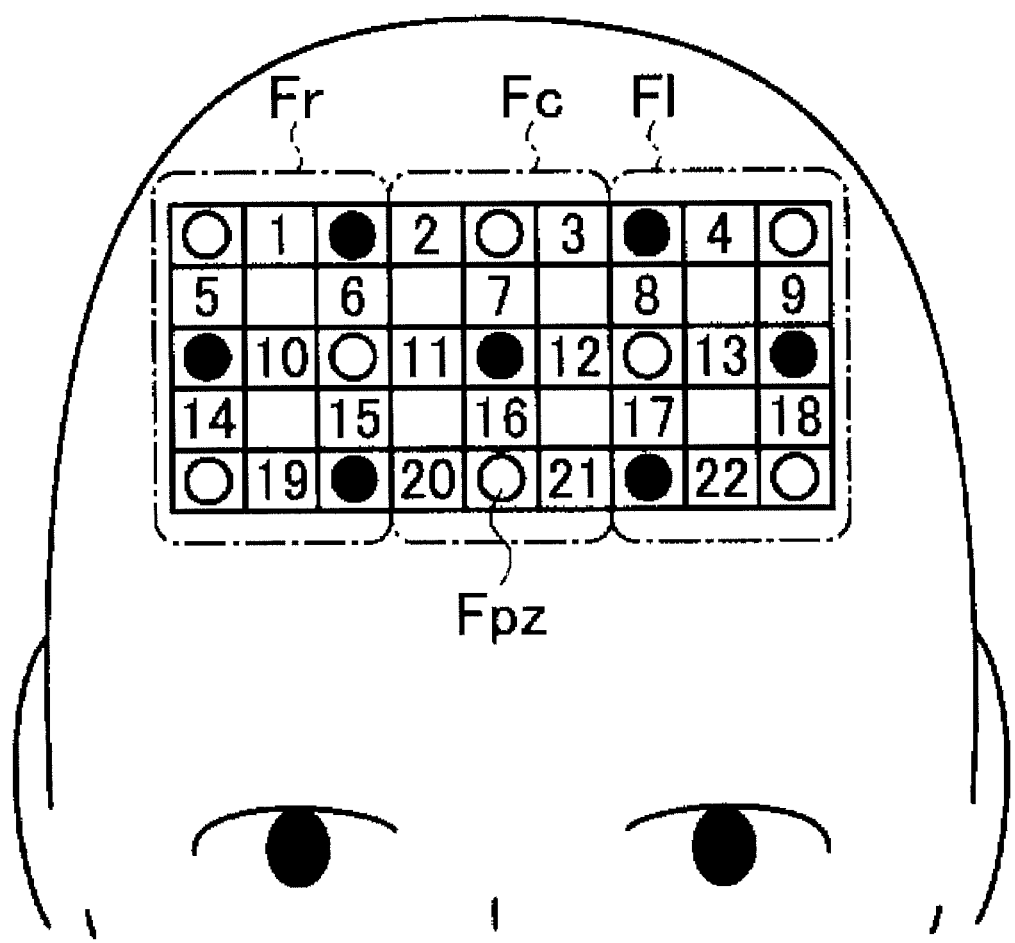
FIG. 2 is an explanatory diagram illustrating a first measurement location using the fNIRS measurement device of FIG. 1.
Figure 3:
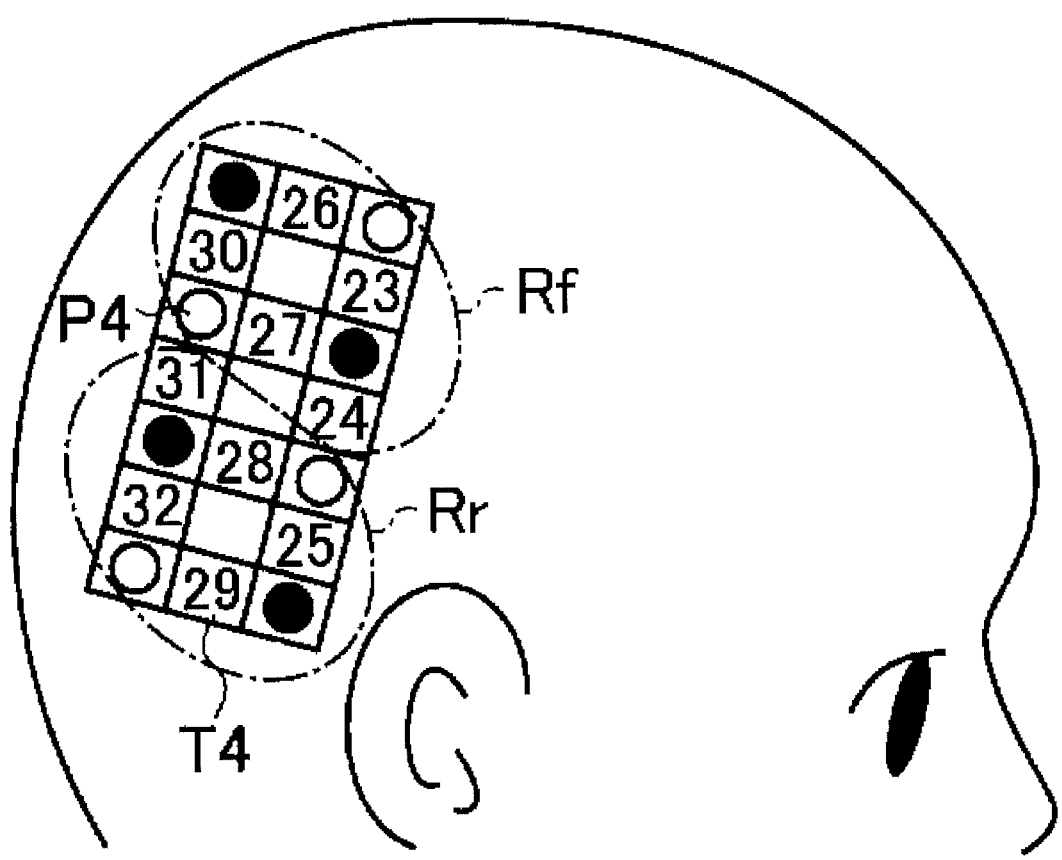
FIG. 3 is an explanatory diagram illustrating a second measurement location using the fNIRS measurement device of FIG. 1.
Figure 4:
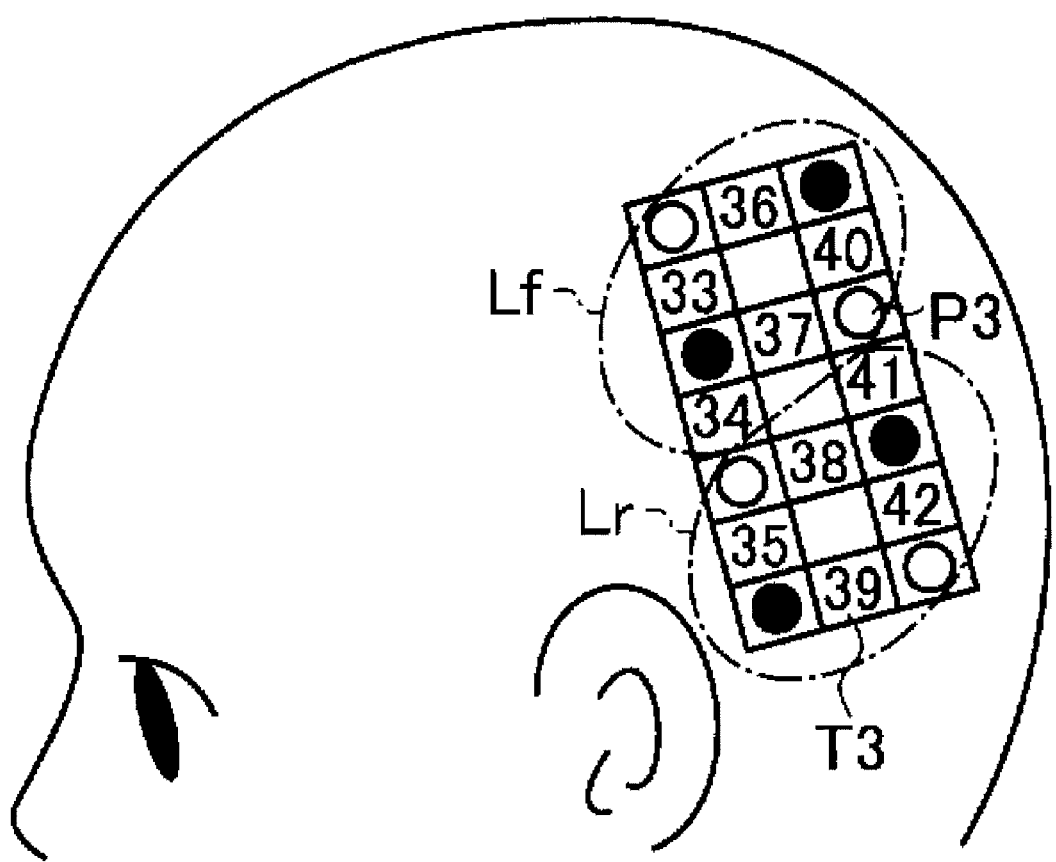
FIG. 4 is an explanatory diagram illustrating a third measurement location using the fNIRS measurement device of FIG. 1.

Such multi-channel fNIRS measurement devices 20, 20a are employed, and in the present exemplary embodiment, as illustrated in FIG. 2 to FIG. 4, cerebral blood flow data of the test subject is measured at plural locations. Note that in FIG. 2 to FIG. 4, the white circular portions are illuminators and the black circular portions are detectors.

As illustrated in FIG. 2, the fNIRS measurement devices 20, 20a measure the cerebral blood flow at 22 channel locations, 1 to 22, in the prefrontal region at a right region Fr, a central region Fc and a left region Fl. Moreover, as illustrated in FIG. 3, in the right temporal lobe the fNIRS measurement devices 20, 20a measure the cerebral blood flow at 10 channel locations, 1 to 10, at a front region Rf and a rear region Rr. Moreover, as illustrated in FIG. 4, in the left temporal lobe the fNIRS measurement devices 20, 20a measure the cerebral blood flow at 10 channel locations, 1 to 10, at a front region Lf and a rear region Lr. The fNIRS measurement devices 20, 20a thereby measure cerebral blood flow at a total of 42 channel locations.

Regarding the attachment positions of each of the probes, with reference to electrode placement of the International 10-20 system in EEG testing, the probe set for the prefrontal region is place horizontally such that the lowest center of the set is superimposed with Fpz, and the probe sets for the left and right temporal lobes and the parietal lobe are placed with reference to the position of the P3, T3 (P4, T4).

The determination device 33 thereby employs the source waveform signal acquisition section 33a to acquire cerebral blood flow data arising from measuring plural sites on the test subject using the fNIRS measurement device 20. Based on the captured cerebral blood flow data from plural sites, the determination device 33 uses the primitive analyzer section 33b to acquire cerebral blood flow data plural regions arising from dividing the plural brain sites into plural regions.

Moreover, the determination device 33 extracts characteristic amounts in the cerebral blood flow data obtained by the characteristic amount extraction section 33c. Then the determination device 33 uses the Bayesian classifier 33d to determine which, out of the 3 categories (3 groups) normal (NC), mild cognitive impairment (MCI), or Alzheimer's disease (AD), applies to the test subject by employing a model (model storage section 33e) that is built in advance for use in cognitive impairment determination.

This determination result is output from the determination device 33 to the display device 40, and displayed on the display device 40.

The learning device 31 uses cerebral blood flow data at plural sites in the brain during cognitive task execution by test subjects for whom it is known whether or not they have impaired cognitive function, and if so at what level. Clinical diagnosis results are accumulated in advance in the data accumulation device 32, and are used to build a model (the clinical model storage sections 31e, 33e) for the determination device 33 to employ in the above cognitive impairment determination.

The data accumulation device 32 uses the source waveform signal acquisition section 32a to acquire from the fNIRS measurement device 20a cerebral blood flow data at plural sites in the brain during cognitive task execution by test subjects for whom it is known whether or not they have impaired cognitive function and if so at what level, and also collects together and accumulates clinical diagnosis results of the test subjects input through an input device, not illustrated in the drawings.

The data accumulation device 32 then, based on the cerebral blood flow data of plural sites that has been accumulated by the primitive analyzer section 32b, acquires cerebral blood flow data of the plural regions of the brain arising from dividing the plural sites. The data accumulation device 32 then uses the characteristic amount extraction section 32c to extract characteristic amounts of cerebral blood flow data.

The data accumulation device 32 uses this processing on plural test subjects with known cognitive function impairment or otherwise, and if so at what level, to acquire cerebral blood flow data characteristic amounts for the plural test subjects, associates these with each other and accumulates the data in the clinical data base 32d.

The learning device 31 employs the clinical data base 31d to accumulate similar data to that accumulated in the clinical data base 32d. Moreover, the learning device 31 uses the characteristic selection section 31a to select, from out of the characteristic amounts thus obtained in the clinical data base 31d, characteristic amount(s) to use in determination. The learning device 31 then uses the learning section 31b to build a model for determining cognitive function impairment, based on the selected characteristic amount(s) and the extracted characteristic amounts.

Detailed explanation next follows regarding building the model for use in cognitive function impairment determination.

In the present exemplary embodiment, as test subjects of known cognitive function impairment or otherwise, and if so at what level, 50 elderly people illustrated in Table 1 (18 men and 32 women aged between 64 and 92) are employed as the test subjects. Table 1 illustrates the breakdown of test subjects by clinical diagnosis group and age category.

In Table 1, the numbers in brackets indicate, sequentially, the numbers in the normal (NC) group, the mild cognitive impairment (MCI) group and the Alzheimer's disease (AD) group. Note that the MCI group corresponds to those patients with a Clinical Dementia Rating (CDR) by a "clinical dementia rating method" of 0.5, and the AD group corresponds to those patients with a CDR of 1.

TABLE 1

|  | Age | | | | | |
| --- | --- | --- | --- | --- | --- | --- |
|  | 64 to 70 | 71 to 75 | 76 to 80 | 81 to 85 | 86 to 92 | Total |
| Men | 3 (2, 0, 1) | 2 (1, 1, 0) | 4 (3, 1, 0) | 7 (1, 4, 2) | 2 (0, 0, 2) | 18 (7, 6, 5) |
| Women | 7 (4, 2, 1) | 7 (5, 2, 0) | 8 (2, 5, 1) | 6 (2, 1, 3) | 4 (1, 3, 0) | 32 (14, 13, 5) |
| Sub Total | 10 (6, 2, 2) | 9 (6, 3, 0) | 12 (5, 6, 1) | 13 (3, 5, 5) | 6 (1, 3, 2) | 50 (21, 19, 10) |

Note that the Clinical Dementia Rating (CDR) is a clinical dementia scale using behavioral observation assessment (an observation method) widely employed throughout the world to evaluate six areas: memory, orientation, judgment and problem solving, community affairs, home and hobbies, and personal care on a 5 step scale. The present exemplary embodiment excludes from the target group any test subjects with a CDR of 2 or above, with moderate to severe dementia. Moreover, an overall evaluation is made of the attitude of the test subject from observation and the content of responses to questions by an operator present during task execution, and test subjects who clearly having a problem following the cognitive tasks are also excluded from the target group.

In the present exemplary embodiment, in order to measure the cerebral function of the elderly people through execution of various cognitive tasks including HDS-R tests, problems for the block design illustrated in FIG. 5 are designed, and measurement is performed simultaneously of voice and fNIRS.

As illustrated in FIG. 5, in the measurements, in a first 10 minute period after start a conversation is held about the place of birth and childhood of the test subject and a Hasegawa test is performed, and in a following 12 minute period cognitive tasks are given of recollection method (1. listening, 2. speaking, 3. seeing) and working memory tasks (1. category recall, 2. reading span test, 3. face recall). In these measurements, in order to get engagement with the tasks, the duration of each task is set at 60 seconds, and a 1 point attention break (rest) of 60 seconds is inserted between each of the cognitive tasks.

Figure 6:
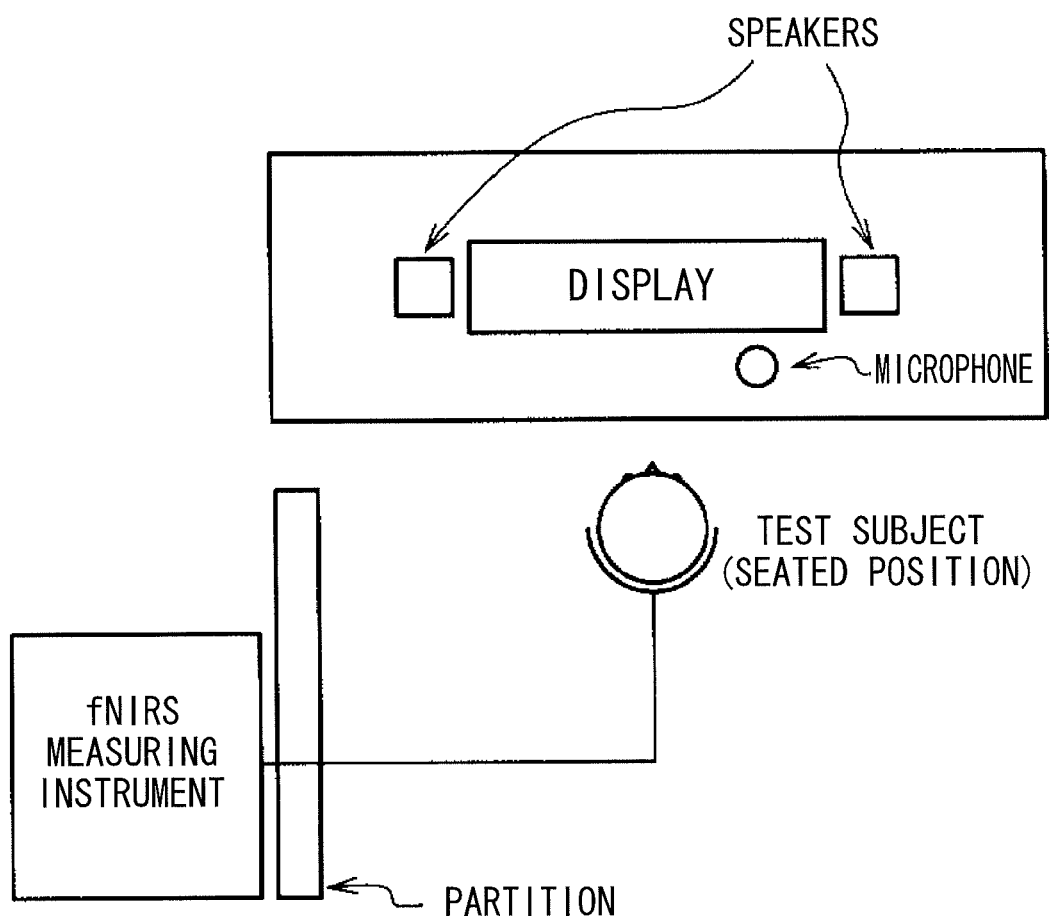
FIG. 6 is an explanatory diagram illustrating an example of a system configuration employed during cerebral blood flow measurement using the fNIRS measurement device of FIG. 1.

Specifically, the tester seats the test subject (subject) directly in front of a task display device (display) in the system environment illustrated in FIG. 6, and places the probes for fNIRS measurement (or electrodes for taking an electroencephalogram (EEG) or the like) on the forehead of the test subject (subject). The cognitive tasks are presented to the test subject (subject) by the display and speakers at the sides.

The test subject executes tasks as they are presented by the display and speakers, and the tester measures the brain activity state during task execution through the fNIRS measurement instrument (or EEG machine or the like).

In the present exemplary embodiment, the fNIRS measurement devices 20, 20a are used, and these fNIRS detectors measure the rate of oxygenated hemoglobin (oxy-Hb), the rate of deoxygenated hemoglobin (deoxy-Hb), and the rate of total hemoglobin (total-Hb). An example is given here in which a measurement signal of oxy-Hb is employed.

In the present exemplary embodiment, as a preparatory investigation, a significant difference test is performed between the 3 groups (NC, MCI, and AD) for all channels (excluding 33CH, 41CH) using fNIRS data (oxy-Hb) during task execution of working memory task 1 (category recall). The test method employs a "t-test", and it is performed as a two-sided test, with a significance level P<0.001, and a Bonferroni correction (1/40).

Figure 7:
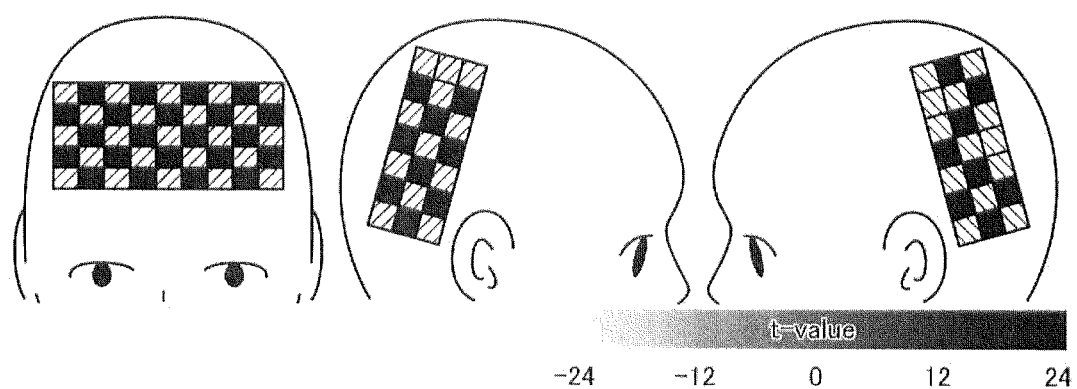
FIG. 7 is an explanatory diagram illustrating an example of first cerebral blood flow measurement results using the fNIRS measurement device of FIG. 1.
Figure 8:
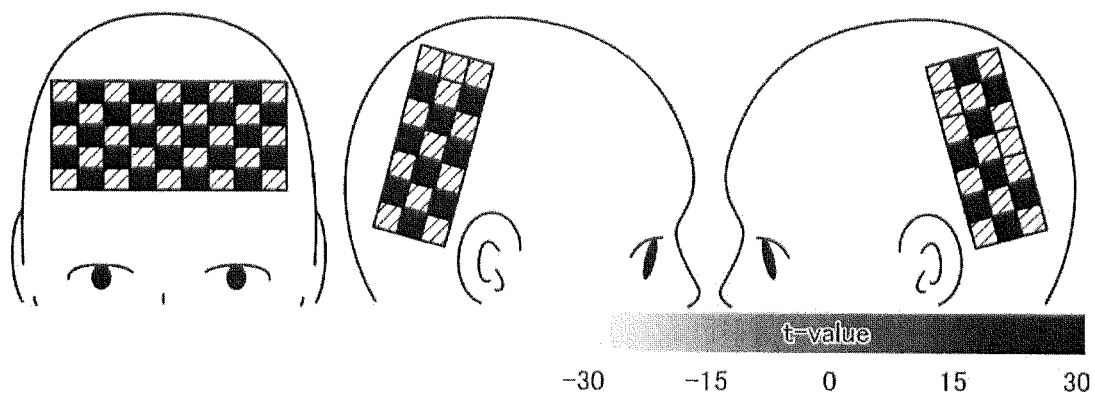
FIG. 8 is an explanatory diagram illustrating an example of second cerebral blood flow measurement results using the fNIRS measurement device of FIG. 1.
Figure 9:
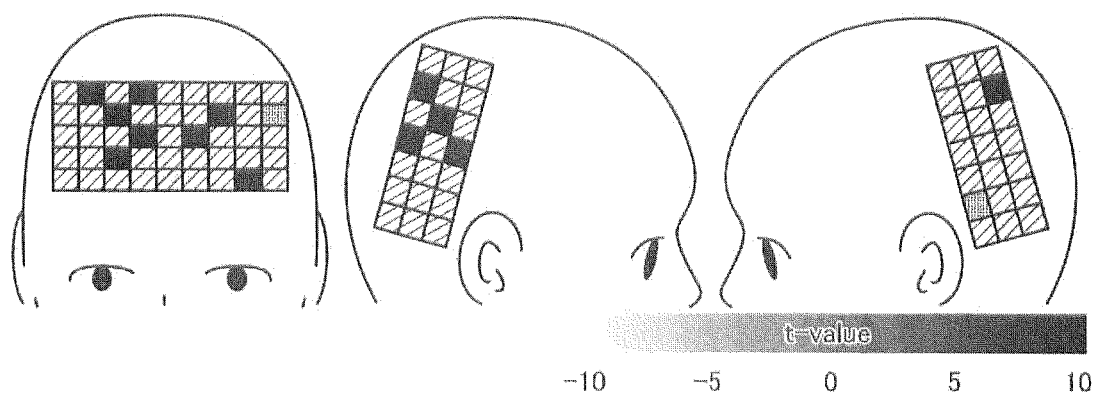
FIG. 9 is an explanatory diagram illustrating an example of third cerebral blood flow measurement results using the fNIRS measurement device of FIG. 1.

FIG. 7 to FIG. 9 illustrate examples in which, for a channel where a significant difference is verified, mapping has been performed to 16 levels of gradation based on t-values. In FIG. 7 to FIG. 9, higher t-value and greater differences are illustrated in denser color, and indicate significant differences.

For someone with dementia, there is a drop in the function of working memory due to impaired cognitive function. As a result, it is possible to confirm that the normal group has significantly more activation than the sick group in the cerebral blood flow of the prefrontal region (see, in FIG. 7 and FIG. 8, the Fr, Fc and Fl regions illustrated in FIG. 2). Moreover, it is possible to confirm that the normal group has significantly more activation than the sick group for the cerebral blood flow in the left and right temporal lobes (the Rf, Rr, Lf and Lr regions illustrated the center and right diagrams in FIG. 7 and FIG. 8 and in FIGS. 3, 4). In addition, as illustrated in FIG. 9, it is possible to confirm that the MCI group that has mild cognitive impairment has slightly, but significantly, more activation in cerebral blood flow compared to the AD group.

Namely, FIG. 7 illustrates channels confirmed to have a significant difference between the normal (NC) group and the mild cognitive impairment (MCI) group. FIG. 8 illustrates channels confirmed to have a significant difference between the normal (NC) group and the Alzheimer's disease (AD) group. FIG. 9 illustrates channels confirmed to have a significant difference between the mild cognitive impairment (MCI) group and the Alzheimer's disease (AD) group.

The results of FIG. 7 to FIG. 9, and in particular the result of FIG. 8, confirm that there is a significant difference in the cerebral blood flow during cognitive task execution between the normal (NC) group and the Alzheimer's disease (AD) group.

This accordingly indicates the possibility or implementing dementia screening using fNIRS data during cognitive task execution. Note that although similar tests are performed on the 3 groups using fNIRS data for the rest intervals immediately preceding the same test execution, there were no significant differences confirmed on any of the channels.

Screening for dementia is accordingly a process that first determines the state of health of cognitive function, then where doubts arise, determines whether there is mild cognitive impairment or dementia according to the level.

Figure 10:
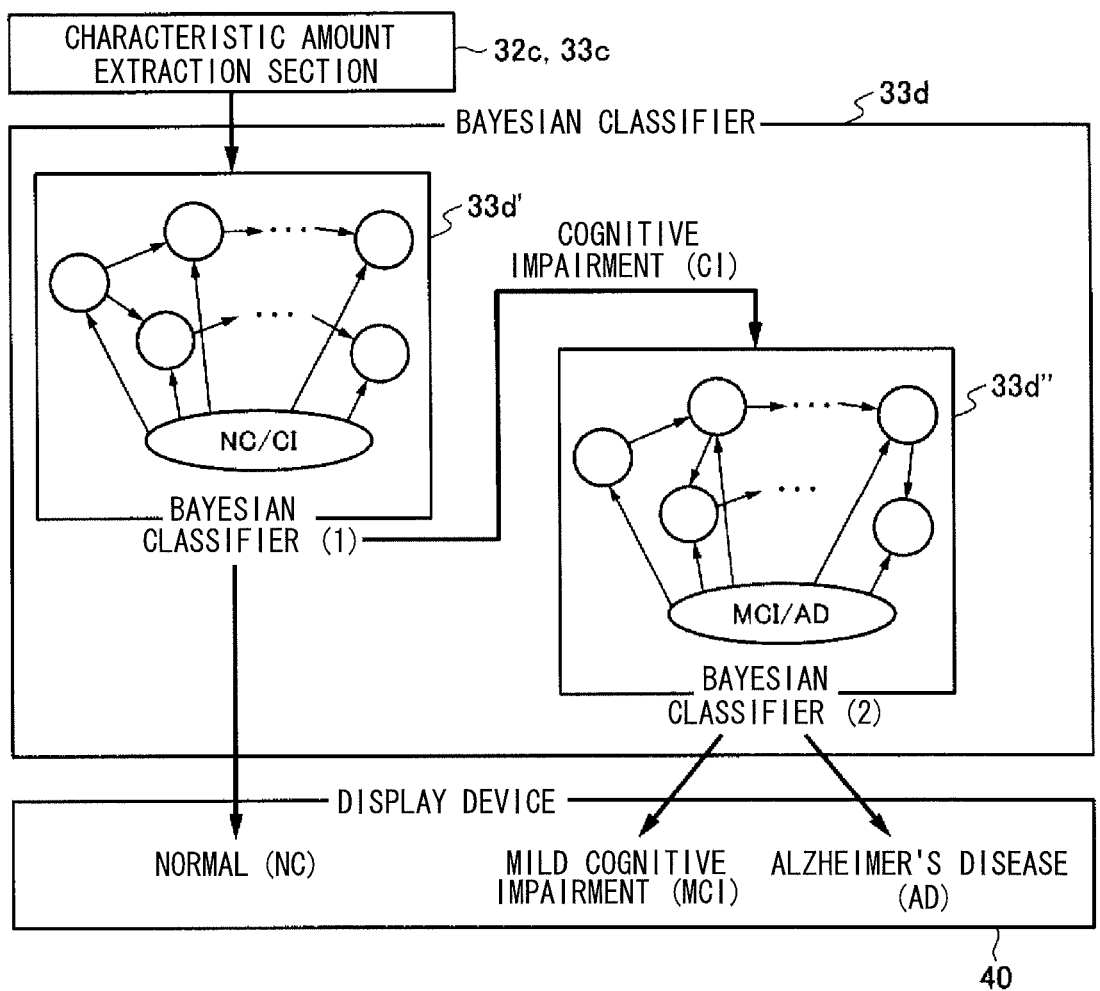
FIG. 10 is a block diagram illustrating an internal configuration of a Bayesian classifier in a cognitive impairment determination apparatus according to a present exemplary embodiment.

However, in the present exemplary embodiment, as illustrated in FIG. 10, the Bayesian classifier 33$d$ is equipped with a Bayesian classifier (1) 33$d'$ and a Bayesian classifier (1) 33$d''$. The Bayesian classifier 33$d$ is thereby employed as a two-stage Naïve-Bayes Classifier to determine 3 groups of the NC group, the MCI group and the AD group from the fNIRS data.

Figure 11:
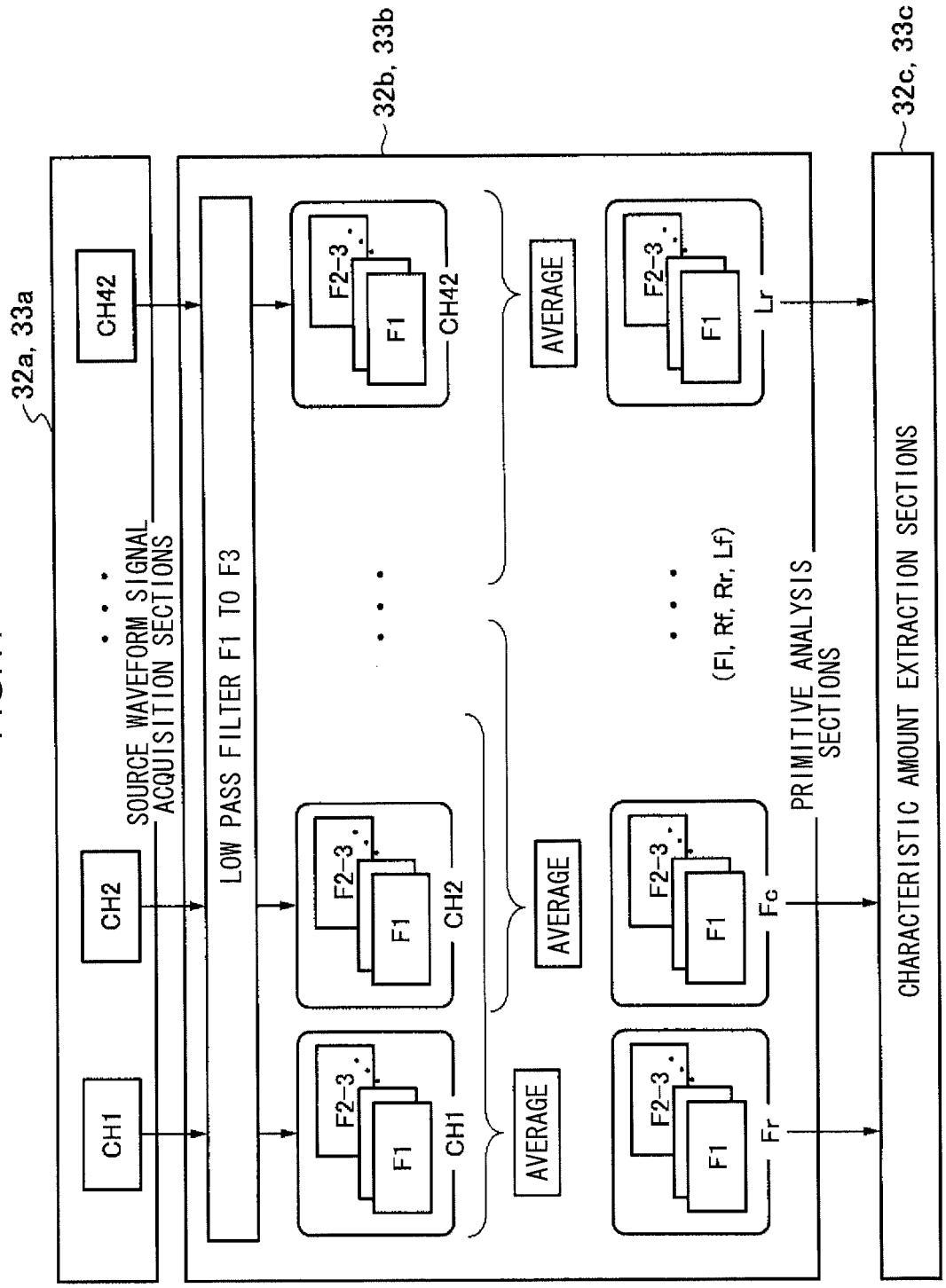
FIG. 11 is a block diagram illustrating an internal configuration of a primitive analysis section in a cognitive impairment determination apparatus according to a present exemplary embodiment.
Figure 12:
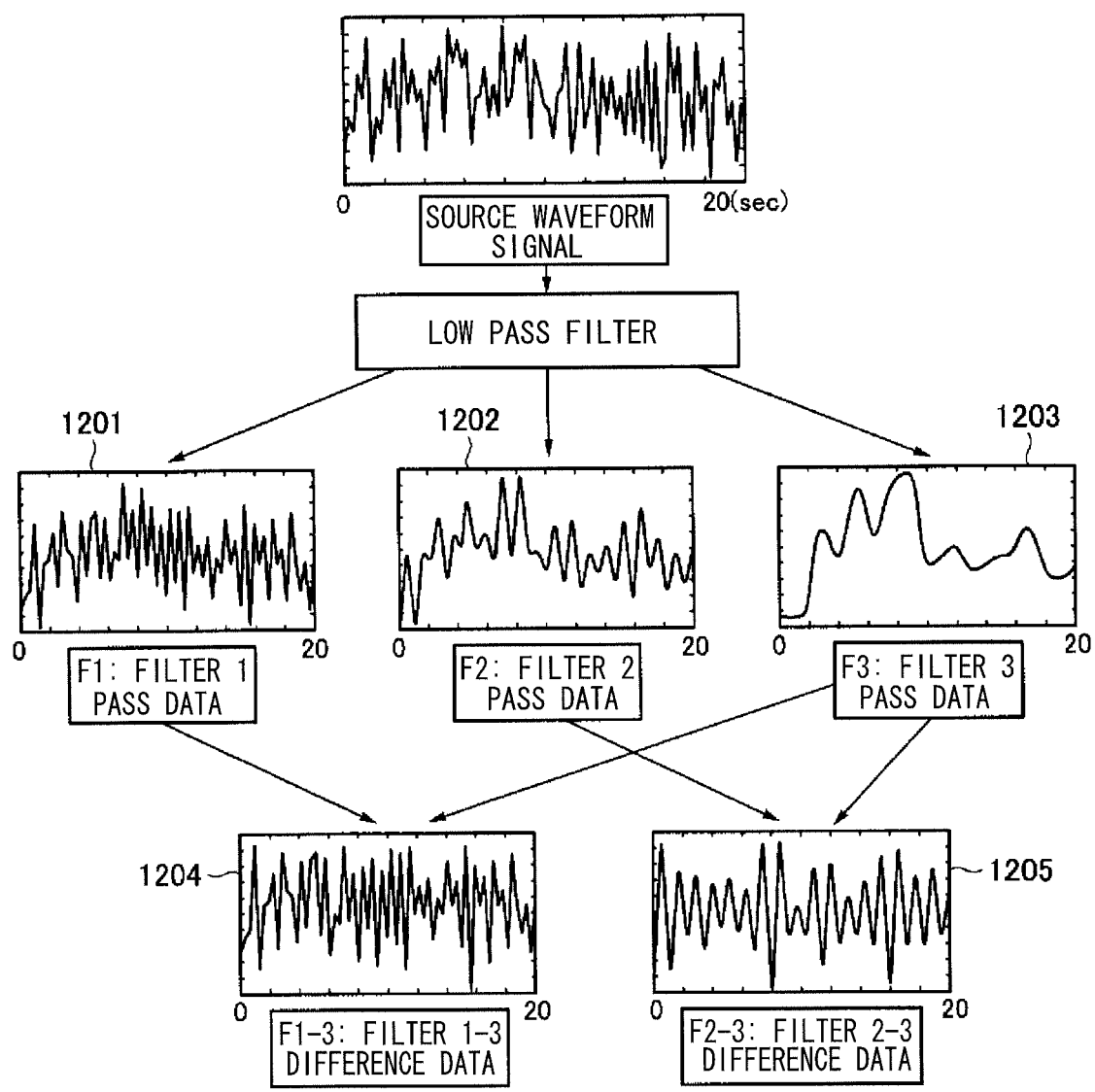
FIG. 12 is an explanatory diagram illustrating an example of processing in the primitive analysis section of FIG. 11.

Explanation next follows regarding the primitive analyzer sections 32$b$, 33$b$, with reference to FIG. 11 and FIG. 12.

The primitive analyzer sections 32$b$, 33$b$ perform primitive analysis on the source waveforms of the fNIRS measurement signals input by the source waveform signal acquisition sections 32$a$, 33$a$ for each of the channels (CH 1 to CH 42). In primitive analysis, noise is removed by applying a low pass filter and a difference filter, and the channels within the region of interest are summed and averaged.

Specifically, as illustrated in FIG. 11, the primitive analyzer sections 32$b$, 33$b$ first perform smoothing by passing the fNIRS signals for each of the channels through 3 low pass filters F1 to F3 (each with $5^{th}$ order Butterworth characteristics).

The blocking frequency of the low pass filter F1 is 1.92 Hz, the blocking frequency of the low pass filter F2 is 0.92 Hz, and the low pass filter F3 is 0.48 Hz.

Moreover, as illustrated in FIG. 12, the primitive analyzer sections 32$b$, 33$b$ add 2 difference filters to the 3 smoothed signals, so as to generate 5 individual fNIRS time series signals per channel. The 5 individual fNIRS time series signals 1201 to 1205 illustrated in FIG. 12 are as follows.

The fNIRS time series signal 1201 is a signal from which noise due mainly to environmental light is removed by the low pass filter F1 (blocking frequency 1.92 Hz).

The fNIRS time series signal 1202 is a signal in which fluctuation components due to pulse and blood pressure (background noise) are extracted by the low pass filter F2 (blocking frequency 0.96 Hz).

The fNIRS time series signal 1203 is a signal from which noise due mainly to movements such as frowning, eyeball movement and head rocking has been removed by the low pass filter F3 (blocking frequency 0.48 Hz).

The fNIRS time series signal 1204 is the difference signal series between the fNIRS time series signal 1201 and the fNIRS time series signal 1203, and the fNIRS time series signal 1204 is a signal that picks up fluctuations.

The fNIRS time series signal 1205 is the difference signal series between the fNIRS time series signal 1202 and the fNIRS time series signal 1203, and the fNIRS time series signal 1205 is a signal that picks up fluctuations.

Next, the primitive analyzer sections 32*b*, 33*b* divide the test brain locations into the following 7 regions, sum the respective fNIRS time series signals in each of the regions and take averages thereof. Specifically, as summed average values for Fr, Fc, Fl, Rf, Rr, Lf, Lr in FIG. 11, the primitive analyzer sections 32*b*, 33*b* perform averaging on each of the 5 signal series described above for the channels within the 7 brain regions (prefrontal region: 3 regions, left and right temporal lobes: 2 regions each).

More precisely, the average value Fr is the average value of the 5 signal series described above for the prefrontal region right side 7 channels (the channels 1, 5, 6, 10, 14, 15, 19).

The average value Fc is the average value of the 5 signal series described above for the prefrontal region center 8 channels (the channels 2, 3, 7, 11, 12, 16, 20, 21).

The average value Fl is the average value of the 5 signal series described above for the prefrontal region left side 7 channels (the channels 4, 8, 9, 13, 17, 18, 22).

The average value Rf is the average value of the 5 signal series described above for the right temporal lobe front 5 channels (the channels 23, 24, 26, 27, 30).

The average value Rr is the average value of the 5 signal series described above for the right temporal lobe rear 5 channels (the channels 25, 28, 29, 31, 32).

The average value Lf is the average value of the 5 signal series described above for the left temporal lobe front 5 channels (the channels 33, 34, 36, 37, 40).

The average value Lr is the average value of the 5 signal series described above for the left temporal lobe rear 5 channels (the channels 35, 38, 39, 41, 42).

The primitive analyzer sections 32*b*, 33*b* input the averaged values of the 5 signal series obtained in this manner for each of the regions to the characteristic amount extraction sections 32*c*, 33*c*.

The characteristic amount extraction sections 32*c*, 33*c* perform characteristic extraction on the 5 signal series for each of the regions obtained by the primitive analyzer sections 32*b*, 33*b* so as to compute the following 11 characteristic amounts. Specifically, from the fNIRS data prepared as described above, the characteristic amount extraction sections 32*c*, 33*c* compute the respective characteristic amounts illustrated in Table 2 as characteristic amounts representing characteristics of cerebral blood flow fluctuation, and compute 11 individual fNIRS characteristic amounts for each of the regions for the test subjects on one task.

Note that the characteristics of fNIRS that are effective for determining cognitive impairment are not yet clear. Even in signal analysis of fNIRS, for example in the frequency regions for each of the waves in brainwaves, such as α, β, γ, δ and θ, definite characteristic amounts such as event-related potentials N100, P300, have not yet been discovered. Therefore, although the present exemplary embodiment utilizes a trial and error approach, it has discovered a data mining approach. For data that has been affected by artifacts and noise to the extent that it cannot be removed by the initial analysis described above, removal is performed in advance by reading the fNIRS signals by eye.

TABLE 2

| Filter Number | fNIRS Characteristic Amount |
| --- | --- |
| Filter 1 (F1) | Amplitude average value (mean) |
| | Fundamental frequency (f0) |
| | Centroid frequency (fc) |

TABLE 2-continued

| Filter Number | fNIRS Characteristic Amount |
| --- | --- |
| Filter 3 (F3) | Amplitude maximum value (max) |
| | Amplitude minimum value (min) |
| | Amplitude variance value (var) |
| | Amplitude average value (mean) |
| | Fundamental frequency (f0) |
| | Gradient of straight line approximation (gr) |
| Filter 1-3 (F1-3) | Amplitude variance value (var) |
| Filter 2-3 (F2-3) | Amplitude variance value (var) |

In Table 2, the filter numbers indicate filter 1 (F1), filter 3 (F3), filter 1-3 (F1-3), filter 2-3 (F2-3), and corresponding fNIRS characteristic amounts are shown.

The filter 1 (F1) is the low pass filter with a blocking frequency of 1.92 Hz. Signals passing through the filter 1 (F1) have noise mainly caused by environmental light removed, and have the widest range of frequency components out of the 5 signal series. Note that filter 1 (F1) includes frequency components of filter 2 (F2).

The filter 2 (F2) is a low pass filter with a blocking frequency of 0.96 Hz. Signals passing through the filter 2 (F2) are signals in which fluctuation components due to pulse and blood pressure (background noise) are extracted, are since these are vital signal components of the autonomic nervous system not directly related to cerebral activity, characteristic amounts are not extracted therefrom.

Filter 3 (F3) is a low pass filter with a blocking frequency of 0.48 Hz. Signals passing through the filter 3 (F3) are signals from which noise due mainly to movements such as forehead opening-closing, eyeball movement and head rocking has been removed, and are signals from out of the 5 signal series with the narrowest frequency components, and are thought to have a comparatively strong relationship to cognitive function.

The filter 1-3 (F1-3) is a signal series of the difference between signals that pass through the filter 1 (F1) and signals that pass through the filter 3 (F3), and attention is paid to fluctuations therein.

The filter 2-3 (F2-3) is a signal series of the difference between signals that pass through the filter 1 (F2) and signals that pass through the filter 3 (F3), and attention is paid to fluctuations therein.

As a fNIRS characteristic amount the amplitude average value (mean) represents the average level of brain activity (activation).

As a fNIRS characteristic amount the fundamental frequency (f0) represents the amplitude frequency (by peak) of brain activity (activation).

As a fNIRS characteristic amount the centroid frequency (fc) represents the amplitude frequency (centroid) of brain activity (activation).

As a fNIRS characteristic amount the amplitude maximum value (max) represents the maximum level of brain activity (activation).

As a fNIRS characteristic amount the amplitude minimum value (min) represents the minimum level of brain activity (activation).

As a fNIRS characteristic amount the amplitude variance value (var) represents the fluctuation in brain activity (activation).

As a fNIRS characteristic amount the amplitude average value (mean) represents the average level of brain activity (activation).

As a fNIRS characteristic amount the gradient of straight line approximation (gr) represents the trend in brain activity (activation).

As a fNIRS characteristic amount the amplitude variance value (var) represents the fluctuation in brain activity (activation).

The characteristic amount extraction sections 32c, 33c perform the processing described above, and store the characteristic amount numerical values (in 77 dimensions) as explanatory variables. Then the data accumulation device 32 then appends clinical diagnosis results (NC: normal, MCI: mild cognitive impairment, AD: Alzheimer's disease) thereto and stores the appended date in the clinical data base 32d.

The learning device 31 accumulates the data stored in the clinical data base 32d by the processing described above in the clinical data base 31d, and uses the data to build the model (Learning).

In the present exemplary embodiment, the learning device 31 uses the 50 persons' (NC: 21 subjects, MCI: 19 subjects, AD: 10 subjects) worth of data to configure the model that estimates a determination result of whether or not cognitive impairment is present and at what level.

Specifically, the learning device 31 configures a Bayesian classifier with the 77 individual fNIRS characteristic amounts extracted from the fNIRS test data of the test subjects as the explanatory variables, and the clinical diagnostic groups as target attributes. Note that a Naïve-Bayesian Classifier is used for the classifier model.

Here, the learning device 31 stores a model that employs 2 determinators in the model storage section 31e, these being a model that employs a determinator $NB_{NC/CI}$ at a first stage to estimate whether or not there is cognitive impairment, and a model that when impairment is estimated employs a determinator $NB_{MCI/AD}$ at a second stage to estimate the level of impairment.

Note that when there are too many characteristic amounts extracted from the data during building the above model, there is a possibility that characteristic amounts are extracted therefrom that are not actually related to determining cognitive impairment, and these conceivably have an adverse influence on the configuration and determination performance of the model.

Thus in the present exemplary embodiment, the learning device 31 uses the characteristic selection section 31a to perform characteristic selection prior to model building. However, the fNIRS characteristics that have a high cause-effect relationship with cognitive impairment in the elderly have not yet been determined, and there is currently no promising theory or prior knowledge for characteristic selection. Moreover, there is a high computational cost from computing all the combinations of extracted characteristic amounts.

Therefore, the characteristic selection section 31a performs characteristic selection using a forward stepwise method as a general applied sequential selection method, as described in for example "Draper, N. and Smith, H.: Applied Regression Analysis (3rd edition), John Wiley & Sons (1998)".

The average values of correct estimation rates for the 2 groups are employed as the characteristic selection criteria in the forward stepwise method.

By using this forward stepwise method, since promising characteristic amounts are automatically selected as the determination criteria for discriminating between normal and cognitive impairment in the Bayesian classifier (1) 33d', the characteristic selection section 31a derives a pseudo optimum characteristic amount combination for discriminating between the 2 groups of the NC group+CI group (the MCI+AD groups).

Since promising characteristic amounts are automatically selected as the determination criteria for discriminating between cognitive impairment levels (mild, dementia) in the Bayesian classifier (2) 33d'', the characteristic selection section 31a derives a pseudo optimum characteristic amount combination for discriminating between the 2 groups of the MCI group and the AD group.

Table 3 illustrates an example in which two promising characteristic amounts have been selected as the determination criteria for discriminating between normal and cognitive impairment in the Bayesian classifier (1) 33d'. Table 3 also illustrates an example in which three promising characteristic amounts have been selected as the determination criteria for discriminating between cognitive impairment levels (mild, dementia) in the Bayesian classifier (2) 33d''.

TABLE 3

| Bayesian Classifier | Selected Characteristic Amount Group |
|---|---|
| Classifier 1 NC/CI | $Fr\_{F3}\_max, Lr\_{F1}\_fc$ |
| Classifier 2 MCI/AD | $Fc\_{F1\text{-}3}\_var, Lf\_{F1}\_mean, Lf\_{F1\text{-}3}\_var$ |

Explanation next follows regarding the characteristic amounts illustrated in Table 3. First, the amplitude maximum value (max) of the signal that has passed through filter 3 (F3) in the region Fr (the 7 channels on the right side of the prefrontal region), and the centroid frequency (fc) of the signal that has passed through the filter 1 (F1) in the region Lr (the 5 channels at the rear of the left temporal lobe) employed as the promising characteristic amounts for determination criteria for discriminating between normal and cognitive impairment in the Bayesian classifier (1) 33d'.

This is due to paying attention to confirmation of a drop in blood flow in the cerebral region of the posterior cingulate gyrus mainly in Alzheimer's disease, as described for example in "Walhovd, K. B., Fjell, A. M., Dale, A. M., McEvoy, L. K., Brewer, J., Karow, D. S., Salmon, D. P., Fennema-Notestine, C., and the Alzheimer's Disease Neuroimaging Initiative: Multi-modal imaging predicts memory performance in normal aging and cognitive decline, Neurobiology of Aging, Vol. 31, No. 7, pp. 1107-1121 (2010)", and to a drop in working memory function accompanying cognitive function impairment. It is confirmed from determination results in the present exemplary embodiment that a cognitive impairment suffer group is determined by a fall in blood flow in the prefrontal region extending the activation cycle at the rear of the temporal regions.

Moreover, the amplitude variance value (var) of the difference signal between signals that have respectively passed through the filters 1, 3 (F1, F3) in the region Fr (the 8 channels in the center portion of the prefrontal region), the amplitude average value (mean) of the signal that has passed through the filter 1 (F1) in the region Lf (the 5 channels at the front of the left temporal lobe), and the amplitude variance value (var) of the difference signal between signals that have respectively passed through the filters 1, 3 (F1, F3) in the region Lf (the 5 channels at the front of the left temporal lobe) are employed as promising characteristic amounts for determination criteria to discriminate between the cognitive impairment levels (mild, dementia) in the Bayesian classifier (2) 33d'''.

This is due to paying attention to confirmation of a fall in cerebral blood flow in the posterior cingulate gyrus and the precuneus as pathological characteristics in the brains of patients on progression for mild cognitive impairment to Alzheimer's disease, as described for example in "Ishiwata 06 Ishiwata, A., Sakayori, O., Minoshima, S., Mizumura, S., Kitamura, S., and Katayama, Y.: Preclinical evidence of Alzheimer changes in progressive mild cognitive impairment: a qualitative and quantitative SPECT study, Acta Neurologica Scandinavica; 114(2):91-6, 2006, Vol. 114, No. 2, pp. 91-96 (2006)". It is confirmed from determination results in the present exemplary embodiment that discrimination is made of Alzheimer's disease from mild cognitive impairment by variance and average value of activation of the parietal region (the left parietal region).

Thus, as illustrated in Table 3, in the present exemplary embodiment the characteristic selection section 31a selects the amplitude maximum value (max) of the signal that has passed through filter 3 (F3) in the region Fr (the 7 channels on the right side of the prefrontal region), and the centroid frequency (fc) of the signal that has passed through the filter 1 (F1) in the region Lr (the 5 channels at the rear of the left temporal lobe) as the two promising characteristic amounts to employ when discriminating between normal and cognitive impairment in the Bayesian classifier (1) 33d'

The characteristic selection section 31a also selects the amplitude variance value (var) of the difference signal between signals that have respectively passed through the filters 1, 3 (F1, F3) in the region Fr (the 8 channels in the center portion of the prefrontal region), the amplitude average value (mean) of the signal that has passed through the filter 1 (F1) in the region Lf (the 5 channels at the front of the left temporal lobe), and the amplitude variance value (var) of the difference signal between signals that have respectively passed through the filters 1, 3 (F1, F3) in the region Lf (the 5 channels at the front of the left temporal lobe) as three characteristic amounts employed for discriminating between the cognitive impairment levels (mild, dementia) in the Bayesian classifier (2) 33d''

The learning device 31 stores in the model storage section 31e the model for determining cognitive impairment in the Bayesian classifier 33d that has been built from the characteristic amounts selected by the characteristic selection section 31a and the characteristic amounts accumulated in the clinical data base 31d.

Specifically, the learning device 31 uses a characteristic amount list as illustrated in Table 3 that has been refined by the learning section 31b, the clinical data base 31d and the characteristic selection section 31a to compute a probabilistic dependency relationship between each of the characteristic amounts, and the characteristic amounts and determination targets. The learning device 31 thereby configures and stores in the model storage section 31e a network structure and parameters (conditional probability distributions) of classification functions in the Bayesian classifier 33d.

The determination device 33 employs the thus built model in the learning device 31 to perform determination of the whether or not the test subject has cognitive impairment. Explanation follows regarding processing performed by the determination device 33 to determine whether or not the test subject has cognitive impairment.

In such cases, an elderly person of unknown cognitive function diagnosis is made to execute the cognitive tasks as illustrated in FIG. 5, in a similar manner to during model building. The determination device 33 determines the cognitive function level of that person from the cerebral blood flow data during execution through the following processing.

Namely, the determination device 33 uses the source waveform signal acquisition section 33a provided to the determination device 33 to acquire cerebral blood flow data for the plural measured locations in the fNIRS measurement device 20, in a similar manner to during model building.

Then the primitive analyzer section 33b performs analysis processing on the acquired cerebral blood flow data from plural locations. Then the characteristic amount extraction section 33c computes the characteristic amounts from the five series for each of the regions obtained by primitive analysis. The Bayesian classifier 33d then uses the model that the learning device 31 has built and that employs the cognitive impairment determinations accumulated in the model storage section 33e to perform determination between NC, MCI and AD for the test subject.

In the determination processing, the determination device 33 first, as illustrated in FIG. 10, uses the Bayesian classifier (1) 33d' to discriminate whether normal (NC), or whether cognitive impairment (CI) is present.

Specifically, the Bayesian classifier (1) 33d' sets computed values corresponding to the selected characteristic amounts as nodes, and executes the NC/CI classification processing. Probability values of classification in the NC group or the CI group are obtained as output thereof.

When the probability of classification in the CI group is estimated to be high, the determination device 33 then employs the Bayesian classifier (2) 33d'' to discriminate whether mild cognitive impairment (MCI) is present or whether Alzheimer's disease (AD) is present, estimating the level of cognitive impairment.

In these cases, similarly to with the Bayesian classifier (1) 33d' as described above, the Bayesian classifier (2) 33d'' sets computed values corresponding to the selected characteristic amounts as nodes, and executes the MCI/AD classification processing. Probability values of classification in the MCI group or the Alzheimer's disease (AD) group are obtained as output thereof.

Explanation follows regarding test results of determination processing by the cognitive impairment determination apparatus according to the present exemplary embodiment.

The test results are results that employ fNIRS data during response to the "Give me as many names of fruits as you can" task executed in the final 20 seconds of the working memory task 1 (category recall), from the cognitive tasks illustrated in FIG. 5 executed by each of the 50 elderly people illustrated in Table 1, as a determination test of NC/MCI/AD.

Leave-one-out cross validation is employed as a validation method. A list of the fNIRS characteristic amounts employed by the Bayesian classifier (1) 33d' and the Bayesian classifier (2) 33d'' are illustrated in Table 3.

Table 4 illustrates cross correlation results of tests in which determination processing is performed by the cognitive impairment determination apparatus according to the present exemplary embodiment on the 50 elderly people.

TABLE 4

| Diagnostic result | Determination Output | | | Detection Rate |
|---|---|---|---|---|
| | NC | MCI | AD | |
| NC | 11 | 7 | 3 | 52.4% |
| MCI | 1 | 14 | 4 | 73.7% |
| AD | 0 | 1 | 9 | 90.0% |
| Accuracy | 91.7% | 63.6% | 56.3% | 68.0% |

The results of Table 4 shown that the determination detection rate of Alzheimer's disease (AD) and the determination accuracy of normal (NC) both exceed 90%. It is clear therefrom that the cognitive impairment determination apparatus according to the present exemplary embodiment does not falsely determine that test subjects belonging to the Alzheimer's disease (AD) group as being normal (NC), and also does not determine test subjects as normal who are actually Alzheimer's disease (AD) suffers (this only occurred for one MCI sufferer).

This result may be said to be a good result from the perspective of a cognitive screening specification. The estimate detection rate for MCI is also 73.7%, and so the performance of the cognitive impairment determination apparatus according to the present exemplary embodiment may be said to be permissible.

Moreover, in the result of the cognitive impairment determination apparatus according to the present exemplary embodiment, 80% of 5 people being falsely determined as having Alzheimer's disease (AD) is an acceptable result.

Figure 13:
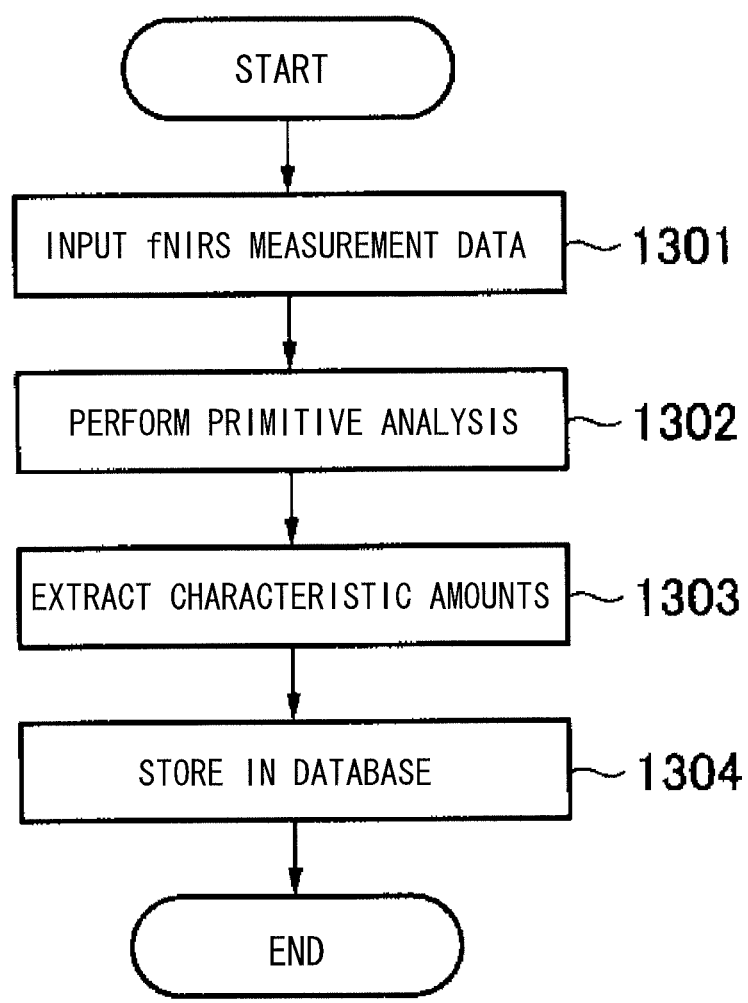
FIG. 13 is a flow chart illustrating a first processing flow executed by a cognitive impairment determination apparatus according to an exemplary embodiment.

Next explanation follows with reference to FIG. 13 and FIG. 15 regarding examples of processing operations by the learning device 31, the data accumulation device 32 and the determination device 33 illustrated in FIG. 1, based on a program stored for example on a computer-readable storage medium. Note that the computer-readable storage medium storing the program may be a portable medium such as a flexible disk, a magneto-optical disk, a ROM or a CD-ROM, or may be a hard disk or the like installed in a computer system.

FIG. 13 illustrates an example of processing operations by the data accumulation device 32, and at step 1301, the data accumulation device 32 acquires the fNIRS measurement data by using the function of the source waveform signal acquisition section 32a.

At step 1302, the data accumulation device 32 performs primitive analysis processing to filter the fNIRS measurement data using the function of the primitive analysis section 32b.

At step 1303, the data accumulation device 32 performs characteristic amount extraction processing on the primitive analysis processed fNIRS measurement data using the function of the characteristic amount extraction section 32c.

At step 1304, the data accumulation device 32 stores in the clinical data base 32d the characteristic amounts for the fNIRS measurement data extracted using the function of the characteristic amount extraction section 32c.

Figure 14:
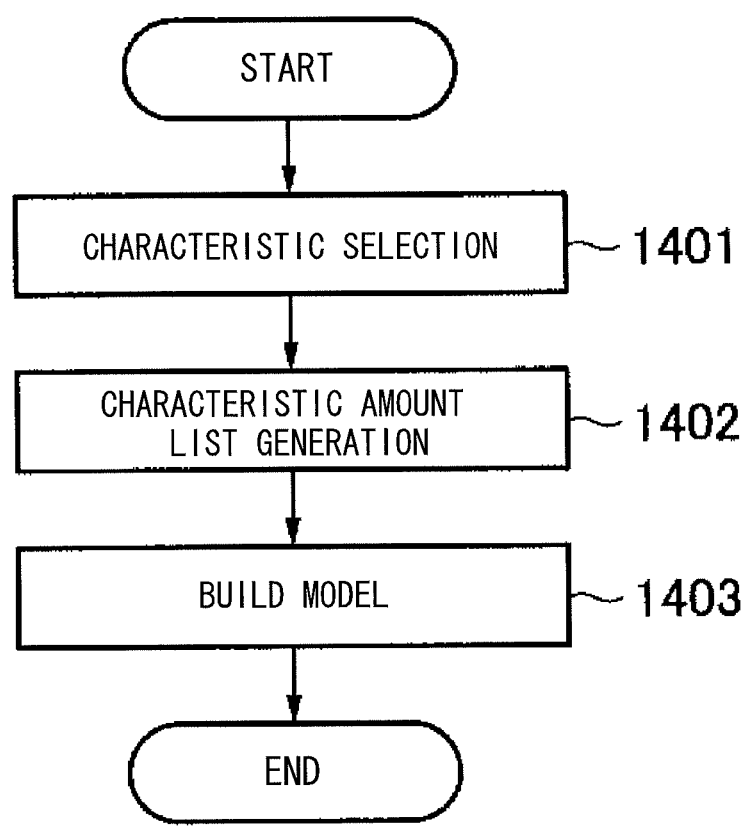
FIG. 14 is a flow chart illustrating a second processing flow executed by a cognitive impairment determination apparatus according to an exemplary embodiment.

FIG. 14 illustrates an example of processing operation of the learning device 31, at step 1401 the learning device 31 uses the function of the characteristic selection section 31a to select characteristic amounts as determination criteria such as for example those illustrated in Table 3 above, from the characteristic amounts for the fNIRS measurement data stored in the clinical data base 31d.

At step 1402, the learning device 31 extracts and lists up the characteristic amounts selected as determination criteria by the function of the characteristic selection section 31a from the clinical data base 31d, and at step 1403 uses the learning section 31b to build the model of a network structure and parameters (conditional probability distributions) for classification functions using as learning data the listed-up characteristic amounts, and stores the model in the model storage section 31e.

FIG. 15 illustrates an example of processing operations of the determination device 33, and at step 1501, the determination device 33 acquires the fNIRS measurement data using the function of the source waveform signal acquisition section 33a.

At step 1502, the determination device 33 using the function of the primitive analysis section 33b to perform primitive analysis processing such as filtering processing on the fNIRS measurement data.

At step 1503, the determination device 33 uses the function of the characteristic amount extraction section 33c to perform characteristic amount extraction processing on the fNIRS measurement data that has been primitive analysis processed.

At step 1504, the determination device 33 uses the function of the Bayesian classifier 33d use the data that has been copied from the model storage section 31e to determine in the model storage section 33e the diagnostic result corresponding to the characteristic amounts of the fNIRS measurement data extracted by the function of the characteristic amount extraction section 33c.

As explained above with reference to each of the drawings, the cognitive impairment determination apparatus 10 according to the present exemplary embodiment acquires cerebral blood flow data as vital signals of plural regions of the brain of a test subject during cognitive task execution, extracts characteristic amounts of the acquired cerebral blood flow data (vital signals), and then determines whether or not the test subject has cognitive impairment based on the extracted characteristic amounts and on pre-prepared data for use in cognitive impairment determination.

Note that, the cognitive impairment determination apparatus 10 generates the data employing cognitive impairment determinations by employing vital signals of plural regions of the brains during cognitive task execution of plural test subjects for whom it is known in advance whether they have cognitive impairment or not, extracting their characteristic amounts, and generation based on the extracted amounts. When doing so, the cognitive impairment determination apparatus 10 selects characteristic amounts to employ in determination from out of the extracted characteristic amounts, and then based on the selected characteristic amounts and the extracted characteristic amounts, configures a model for determining cognitive impairment as data for use in determination.

The cognitive impairment determination apparatus 10 hence, by acquiring vital signals of plural regions of the brain of a test subject during cognitive task execution and extracting characteristic amounts of the vital signals, is thereby able to determine whether or not the test subject has cognitive impairment based on these characteristic amounts and on pre-derived data for use in cognitive impairment determination, thereby enabling early stage screening of cognitive function.

Note that in the exemplary embodiment described above an example is given in which a model for determining cognitive function is built in the cognitive impairment determination apparatus, however an apparatus for building a model to determine cognitive impairment (the learning device 31 and the data accumulation device 32) may be provided separately to the cognitive impairment determination apparatus. For example, a cognitive impairment determination system may be built with plural of the cognitive impairment determination apparatuses provided that respectively transmit data for model building through a network to a center (a function serving as an apparatus for building a model for determining cognitive impairment), and with the data accumulated in this manner and the model built on the center side, the cognitive impairment determination apparatus (the determination device 33) then receives the model from the center during cognitive impairment determination, so as to perform cognitive impairment determination based thereon.

Moreover, in the present exemplary embodiment, although an example has been given in which cerebral blood flow data obtained with an fNIRS measuring instrument is used as vital signals of the brain, configuration may be made, for example, to employ brainwaves obtained such as by an EEG machine.

Moreover, in the present exemplary embodiment, an fNIRS measuring instrument manufactured by Shimadzu Corporation® is employed, however there is no limitation thereto and another NIRS measuring instrument may be employed.

Moreover, although in the present exemplary embodiment as test subjects a collection of 50 elderly people of ages from 64 to 92 are employed, it is possible to perform determination of dementia risk by classifying test subjects in to plural groups in advance. For example, cerebral blood flow data may be collected in advance from elderly people, and then classified into plural groups according to similarities therein. Then, by calculating weightings based on the degree of similarity of distributions between the data of an unknown determination subject and these groups, a weighted distribution (individual difference application distribution) applicable to determination of the determination subject is pseudo-calculated to give a calculation method to execute determination calculation based on this weighted distribution. It is thereby possible to determine a cognitive impairment risk appropriate to individual differences in cerebral blood flow data of elderly people.

Note that the plural groups described above are generally an appropriate number of groups for a classification means based on similarities in acquired cerebral blood flow data, however other than this, it is also possible to absorb gender differences and age differences by for example using 2 groups of men/women, and fixing plural groups by age (age bands).

Moreover, in the present exemplary embodiment, the primitive analysis sections 32b, 33b respectively average the fNIRS time series signals in each of the regions arrived at by dividing the measurement brain sites into 7 regions (3 regions in the prefrontal region and 2 regions in each of the left and right temporal lobes). However, for example a blind data source separation technology, such as principal component analysis (PCA), independent component analysis (ICA), singular value decomposition (SVD), or non-negative matrix factorization (NMF), may be applied to separate and extract promising signals for determining cognitive impairment from within each region. There is an expectation of even higher performance by employing such computation technology.

In the present exemplary embodiment, the learning device 31 performs characteristic amount selection processing operation using the characteristic selection section 31a, and performs characteristic selection using a forward stepwise method as a general applied sequential selection method, however there is no limitation thereto. The learning device 31 may for example perform characteristic selection by employing a step-up procedure, a step-down procedure, or a serial selection method such as a step-up, step-down method, or by employing a simultaneous selection method such as a Genetic Algorithm (GA), Particle Swarm Optimization (PSO), or a technology employing evolutionary computation such as Evolutionary Stable Strategy (ESS) or Differential Evolution (DE).

Moreover, in the present exemplary embodiment, the determination device 33 employs a Naïve-Bayesian classifier as a classification model for determining cognitive impairment, however there is no limitation thereto. For example, classification type estimations methods such as Bayesian networks, canonical discriminant analysis, linear discriminant analysis, neural networks, Naive-Bayes methods or support vector machines (SVM), or numerical type estimation methods such as multiple regression analysis, ridge regression, support vector regression (SV regression) or Kernel regression analysis.

For example, as a classification type computation method, a risk of dementia is determined from voice data of elderly people by classification into one of the 3 groups normal (NC), mild cognitive impairment (MCI) or Alzheimer's disease (AD). Moreover, as a numerical computation method, numerical values corresponding to point scores (0 to 30) of a cognitive function test such as Hasegawa scoring are output, and the risk of dementia determined by the magnitude of the numerical values.

Moreover, it is possible to provide the program of the present invention stored on a storage medium. A computer-readable storage medium according to the present invention is stored with a program that causes a computer to function as a computer to function as: a data acquisition section that acquires vital signal data at a predetermined brain location of a test subject measured whilst being given a task that causes brain activation; a characteristic amount extraction section that extracts characteristic amounts of the vital signal data acquired by the data acquisition section; and a determination section that determines a level of cognitive impairment of the test subject based on the characteristic amount extracted by the characteristic amount extraction section and based on pre-derived data for use in determination of cognitive impairment.

The disclosure of Japanese patent application 2011-121241 is incorporated by reference in its entirety in the present specification.

All cited documents, patent applications and technical standards mentioned in the present specification are incorporated by reference in the present specification to the same extent as if the individual cited document, patent application, or technical standard was specifically and individually indicated to be incorporated by reference.

The invention claimed is:

1. A cognitive impairment determination apparatus comprising:
    a data acquisition section that acquires vital signal data at each of predetermined brain locations, for a test subject whose level of cognitive impairment is unknown, measured whilst the test subject is being given a task that causes brain activation;
    a characteristic amount extraction section that extracts a plurality of vital characteristic amounts from the respective vital signal data of the test subject of the unknown cognitive impairment level acquired by the data acquisition section; and
    a determination section that determines a level of cognitive impairment of the test subject of the unknown cognitive impairment level based on
        (1) at least one determination characteristic amount configured from a combination of a brain location and a vital characteristic amount of the vital signal data of the brain location, for use in determining a level of cognitive impairment, pre-selected based on (a) the plurality of vital characteristic amounts extracted respectively from vital signal data at each of the pre-determined brain locations of a plurality of test subjects whose level of the cognitive impairment is known, and (b) levels of cognitive impairment of each test subject, wherein the determination characteristic amount is obtained from the plurality of vital characteristic amounts of the respective vital signal data of each of the brain locations of the test subject extracted by the characteristic amount extraction section, and
        (2) a model for determining the cognitive impairment level corresponding to the determination characteristic amount, the model being pre-built using as learning data (a) the selected determination characteristic amounts for each of the plurality of test subjects, as obtained from the plurality of vital characteristic amounts of the respective extracted vital signal data of each of the brain locations of the plurality of test subjects, and (b) the respective cognitive impairment levels of each of the plurality of test subjects.

2. The cognitive impairment determination apparatus of claim 1, wherein:
the vital signal data is cerebral blood flow data measured from blood flow at the predetermined brain locations.

3. The cognitive impairment determination apparatus of claim 1, wherein:
the vital signal data is cerebral blood flow data from measuring hemoglobin flow rates using an NIRS device with a prefrontal region, a left temporal lobe, a right temporal lobe, a left parietal lobe and a right parietal lobe respectively serving as the predetermined brain locations.

4. The cognitive impairment determination apparatus of claim 1, wherein:
the vital signal data is cerebral blood flow data from measuring hemoglobin flow rates for each region using an NIRS device with a right region, a central region and a left region in a prefrontal region serving as predetermined brain locations, and a specific region in a left parietal lobe and a specific region in a left temporal lobe serving as predetermined brain locations, and a specific region in a right parietal lobe and a specific region in a right temporal lobe respectively serving as predetermined brain locations.

5. The cognitive impairment determination apparatus of claim 1, further comprising:
a primitive analysis section that performs noise removal on the vital signal data using a plurality of low pass filters, wherein the plurality of low pass filters includes a first filter employed to remove noise including noise from environmental light, a second filter employed for extracting fluctuation components including brainwaves and blood pressure, and a third filter employed to remove noise due to movement including jaw movement and eyeball movement; wherein in the characteristic amount extraction section,
the primitive analysis section extracts, as characteristic amounts of the vital signal data,
an amplitude average value, a fundamental frequency and a centroid frequency for the vital signal data from which noise has been removed using the first filter,
an amplitude maximum value, an amplitude minimum value, an amplitude variance value, an amplitude average value, a fundamental frequency and a gradient of straight line approximation for vital signal data from which noise has been removed using the third filter,
an amplitude variance value of difference data between the vital signal data from which noise has been removed using the first filter and the vital signal data from which noise has been removed using the third filter, and
a variance value of difference data between the vital signal data from which noise has been removed using the second filter and the vital signal data from which noise has been removed using the third filter; and
the determination section performs determination of the cognitive impairment level of the test subject on the basis of characteristic amounts extracted by the data characteristic amount extraction section.

6. The cognitive impairment determination apparatus of claim 1, further comprising:
a known data acquisition section that acquires vital signal data that is measured whilst a plurality of test subjects whose levels of cognitive impairment are known based on clinical diagnosis results are being given a task that causes brain activation, measured at each of the predetermined brain locations of the plurality of test subjects;
a known data characteristic amount extraction section that extracts a plurality of vital characteristic amounts from the respective vital signal data at each of the brain locations of the plurality of test subjects acquired by the known data acquisition section;
a selection section that based on the plurality of vital characteristic amounts of respective vital signal data at each of the brain locations of the plurality of test subjects extracted by the known data characteristic amount extraction section and based on the clinical diagnosis result of each of the test subjects, selects at least one of the determination characteristic amounts to use in determining a level of cognitive impairment; and
a learning section that employs as learning data the at least one selected determination characteristic amount for each of the plurality of test subjects obtained from the plurality of vital characteristic amounts for each respective vital signal data for each of the brain locations of the plurality of test subjects extracted by the known data characteristic amount extraction section, and the cognitive impairment level of the respective clinical diagnosis results for each of the plurality of test subjects, to build a model for determining a level of the cognitive impairment corresponding to the determination characteristic amount; wherein
the determination section determines a level of cognitive impairment of a test subject of unknown level of the cognitive impairment based on the at least one determination characteristic amount selected by the selection section obtained from the plurality of vital characteristic amounts for each respective vital signal data for each brain location of the test subject extracted by the characteristic amount extraction section and based on the model pre-built by the learning section.

7. The cognitive impairment determination apparatus of claim 6, wherein:
the determination section comprises a plurality of determination sections that determine the cognitive impairment level in a plurality of stages;
the selection section selects at least one of the determination characteristic amounts to use in the determination section for stage determination of the cognitive impairment level for each of the respective plurality of determination sections; and
the learning section builds the model to use in the determination section for stage determination of the cognitive impairment level for each of the respective plurality of determination sections.

8. The cognitive impairment detection apparatus of claim 1, wherein:
the determination section determines a level of cognitive impairment of the test subject of the unknown cognitive impairment level based on
(1) the determination characteristic amount pre-selected based on (a) the plurality of vital characteristic amounts extracted respectively from vital signal data at each of the predetermined brain locations of a plurality of test subjects whose levels of the cognitive impairment are known based on clinical diagnosis results, and (b) clinical diagnosis results of each test subject, and (2) the model pre-built using as learning data (a) the selected determination characteristic amounts for each of the plurality of test subjects, as obtained from the plurality of vital characteristic amounts of the respective vital signal data of each of the brain locations of the plurality of test subjects, and (b) the respective cognitive impairment levels of the clinical diagnosis results of each of the plurality of test subjects.

9. A cognitive impairment determination system comprising:
   a determination data generation device including
      a known data acquisition section that acquires vital signal data at each of predetermined brain locations, measured whilst a plurality of test subjects whose levels of cognitive impairment are known based on clinical diagnosis results are being given a task that causes brain activation,
      a known data characteristic amount extraction section that extracts a plurality of vital characteristic amounts of the vital signal data acquired by the known data acquisition section at each of the brain locations of the plurality of test subjects, and
      a selection section that, based on the plurality of vital characteristic amounts of respective vital signal data at each of the brain locations of the plurality of test subjects extracted by the known data characteristic amount extraction section and based on the clinical diagnosis result of each of the test subjects, selects at least one determination characteristic amount configured from a combination of a brain location and a vital characteristic amount of vital signal data of the brain location to use in determining a level of cognitive impairment, and
      a learning section that employs, as learning data, the at least one selected determination characteristic amount for each of the plurality of test subjects obtained from the plurality of vital characteristic amounts for each respective vital signal data for each of the brain locations of the plurality of test subjects extracted by the known data characteristic amount extraction section, and the cognitive impairment level of the respective clinical diagnosis results for each of the plurality of test subjects, to build a model for determining a level of cognitive impairment corresponding to the determination characteristic amount; and
   a cognitive impairment determination apparatus including
      a data acquisition section that acquires vital signal data at each of the predetermined brain locations for a test subject whose level of the cognitive impairment is unknown measured whilst being given the task,
      a characteristic amount extraction section that extracts the plurality of vital characteristic amounts from the respective vital signal data of the test subject of the unknown cognitive impairment level acquired by the data acquisition section, and
      a determination section that determines a level of cognitive impairment of the test subject of the unknown cognitive impairment level based on a determination characteristic amount obtained from the plurality of vital characteristic amounts for each respective vital signal data for each of the brain locations of the test subject extracted by the characteristic amount extraction section and selected by the selection section and based on the model pre-built by the learning section.

10. A non-transitory computer readable medium storing a program causing a computer to execute a process for cognitive impairment determination, the process comprising:
   acquiring vital signal data at each of predetermined brain locations, of a test subject whose level of cognitive impairment is unknown, measured whilst the test subject is being given a task that causes brain activation;
   extracting a plurality of vital characteristic amounts from the acquired respective vital signal data of a test subject whose level of the cognitive impairment is unknown; and
   determining a level of cognitive impairment of the test subject of the unknown cognitive impairment level based on
      (1) at least one determination characteristic amount configured from a combination of a brain location and a vital characteristic amount of the vital signal data of the brain location, for use in determining a level of cognitive impairment, pre-selected based on (a) the plurality of vital characteristic amounts extracted respectively from vital signal data at each of the predetermined brain locations of a plurality of test subjects whose levels of the cognitive impairment are known, and (b) levels of cognitive impairment of each test subject, wherein the determination characteristic amount is obtained from the plurality of vital characteristic amounts of the respective vital signal data of each of the brain locations of the test subject extracted by the characteristic amount extraction section, and
      (2) a model for determining the cognitive impairment level corresponding to the determination characteristic amount, the model being pre-built using as learning data (a) the selected determination characteristic amounts for each of the plurality of test subjects, as obtained from the plurality of vital characteristic amounts of the respective extracted vital signal data of each of the brain locations of the plurality of test subjects, and (b) the respective cognitive impairment levels of the plurality of test subjects.

* * * * *